(12) United States Patent
Wangh

(10) Patent No.: US 6,878,546 B2
(45) Date of Patent: Apr. 12, 2005

(54) PRODUCT AND METHOD FOR SWELLING A CELL NUCLEUS WITHOUT DNA REPLICATION

(75) Inventor: Lawrence J. Wangh, Auburndale, MA (US)

(73) Assignee: Brandeis University, Waltham, MA (US)

(*) Notice: Subject to any disclaimer, the term of this patent is extended or adjusted under 35 U.S.C. 154(b) by 380 days.

(21) Appl. No.: 10/098,247

(22) Filed: Mar. 14, 2002

(65) Prior Publication Data

US 2002/0132344 A1 Sep. 19, 2002

Related U.S. Application Data

(63) Continuation of application No. 09/226,766, filed on Jan. 6, 1999, which is a continuation of application No. 09/050,380, filed on Mar. 30, 1998, now Pat. No. 6,245,567, which is a continuation of application No. 08/455,981, filed on May 31, 1995, now Pat. No. 5,773,217, which is a division of application No. 08/190,771, filed on Feb. 1, 1994, now Pat. No. 5,651,992, which is a continuation-in-part of application No. 08/013,039, filed on Feb. 3, 1993, now Pat. No. 5,480,772.

(51) Int. Cl.$^7$ .............................. C12N 5/00; C12N 5/02
(52) U.S. Cl. ....................... 435/408; 435/325; 435/375
(58) Field of Search ................................ 435/408, 325, 435/375

(56) References Cited

U.S. PATENT DOCUMENTS

| | | | |
|---|---|---|---|
| 4,722,598 A | 2/1988 | Ford ............................ | 359/398 |
| 4,865,812 A | 9/1989 | Kuntz et al. .................... | 422/99 |
| 4,873,191 A | 10/1989 | Wagner et al. ............ | 435/172.3 |
| 5,358,847 A | 10/1994 | Brown ............................ | 435/6 |
| 5,480,772 A * | 1/1996 | Wangh ............................ | 435/2 |
| 5,496,720 A | 3/1996 | Susko-Parrish et al. .. | 435/240.2 |
| 5,651,992 A * | 7/1997 | Wangh ......................... | 424/520 |
| 5,773,217 A * | 6/1998 | Wangh ............................ | 435/6 |

FOREIGN PATENT DOCUMENTS

| | | |
|---|---|---|
| WO | WO 97/07668 | 3/1997 |
| WO | WO 97/37009 | 10/1997 |
| WO | WO 98/07841 | 2/1998 |
| WO | WO 98/27214 | 6/1998 |

OTHER PUBLICATIONS

Fulka et al (1998) BioEssays 20, 847–851.*
Kono (1997) Reviews Reproduc. 2, 74–80.*
Wolf et al (1998) J. Biotech. 65, 99–110.*
Kono. Nuclear Transfer and Reprogramming. Reviews of Reproduction. 1997, vol. 2, pp. 74–70.*
Fluka et al. Cloning by Somatic Cell Nuclear Transfer. BioEssays. 1998. Vo. 20, pp. 847–851.*
Dinnyes et al. Somatic Cell Nuclear Transfer: Recent Progress and Challenges. Cloning and Stem Cells. 2002, vol. 4, No. 1, pp. 81–90.*

Bianchi et al., "Isolation of Fetal DNA From Nucleated Erythrocytes in Maternal Blood," Proc. Natl. Acad. Sci. USA 87:3279–3283 (1990).
Brown et al., "Chromatin Decondensation And DNA Synthesis In Human Sperm Activated In Vitro By Using *Xenopus Laevis* Egg Extracts," J. Exp. Zool. 242:215–231 (1987).
Brown et al., J. Cell Biology 111:2839 (1990).
Lohka et al., "Roles of Cytosol And Cytoplasmic Particles In Nuclear Envelope Assembly And Sperm Pronuclear Formation In Cell–Free Preparations From Amphibian Eggs," J. Cell Biology 98:1222–1230 (1984).
Mohbubani et al., "DNA Replication Initiates At Multiple Sites On Plasmid DNA In Xenopus Egg Extracts," Nucleic Acids Research vol. 20 No. 7 1457–1462 (1992).
Meier et al., "The Role of Lamin LIII In Nuclear Assembly And DNA Replication, In Cell–Free Extracts of Xenopus Eggs," J. Cell Science 98:271–279 (1991).
Mills et al., "Replication Occurs At Discrete Foci Spaced Throughout Nuclei Replicating In Vitro," J. Cell Science 94:471–477 (1989).
Murray et al., "Cyclin Synthesis Drives The Early Embryonic Cell Cycle," Nature 339:275–280 (1989).
Newport, "Nuclear Reconstitution In Vitro: Stages of Assembly Around Protein–Free DNA," Cell 48:205–217 (1987).
Ohsumi et al., "Chromosome Condensation In Xenopus Mitotic Extracts Without Histone H1," Science 262:2033–2035 (1993).
Pardee, "G$_1$ Events And Regulation of Cell Proliferation," Science vol. 246 No. 4930 pp. 603–640 (1989).
Philpott et al., "Sperm Decondensation In Xenopus Egg Cytoplasm Is Mediated By Nucleoplasmin," Cell 65:569–578 (1991).
Philpott et al., "Nucleoplasmin Remodels Sperm Chromatin In Xenopus Egg Extracts," Cell 69:759–767 (1992).
Sheehan et al., "Steps In The Assembly of Replication–Competent Nuclei In A Cell–Free System From Xenopus Eggs," J. Cell Biology 106:1–12 (1988).
Sieeman et al., "Pattens of DNA Replication in Drosophilia Polytene Nuclei Replicating In Xenopus Egg And Oocyte Extracts," J. Cell Science 101:509–515 (1992).*
Smythe et al., "Coupling of Mitosis To The Completion of S Phase In Xenopus Occurs via Modulation of The Tyrosine Kinase That Phosphorylates P34$^{cdc2}$," Cell 68:787–797 (1992).*

(Continued)

Primary Examiner—Peter Paras, Jr.
Assistant Examiner—Valarie Bertoglio
(74) Attorney, Agent, or Firm—Fish & Richardson P.C.

(57) ABSTRACT

The present invention concerns products and methods particularly useful for activating and analyzing non-dividing cell nuclei. The featured products include activating egg extracts, cytostatic factor (CSF) extracts, kits containing these extracts, and a microchamber microscope slide useful in analyzing nucleus activation.

16 Claims, 4 Drawing Sheets

OTHER PUBLICATIONS

Biosis Abstract 89: 124166 (abstract of Coppock et al., 1989, reference BS above).

Chemical Abstracts 78: 121703 (abstract of Masui, 1972, reference ER above).

Chemical Abstracts 92: 38124 (abstract of Meyerehof et al. 1979, reference FQ above).

Medline Abstract 84143479 (abstract of Riabova et al. 1984, reference GR above).

Medline Abstract 86152393 (abstract of Mausi et al, 1984, reference ES above).

Lohka et al., "Effects of $Ca^2$ Ions on the Formation of Metaphase Chromosomes and Sperm Pronuclei in Cell–free Preparations from Unactivated Rana Pipiens Eggs," Developmental Biology 103:434–442 (1984) [previously submitted as reference QQ above, but crossed off by examiner].

Wangh, L.J. "Injection of Xenopus Eggs before Activation, Achieved by Control of Extracellular Factors, Improves Plasmid DNA Replication after Activation," Journal of Cell Science 933: 1–8 (1989).

Lohka et al., "Induction of Nuclear Envelope Breakdown, Chromosome Condensation, and Spindle Formation in Cell–free Extracts," The Journal of Cell Biology, 101:518–523 (1985).

Blank et al., "Reactivation of DNA Replication in Erythrocyte Nuclei by Xenopus Egg Extract Involves Energy–Dependent Chromatin Decondensation and Changes in Histone Phosphorylation," Experimental Cell Research, 202:224–232 (1992).

Dasso, et al., "Completion of DNA Replication is Monitored by a Feedback System That Controls the Initiation of Mitosis In Vitro: Studies in Xenopus," Cell, 61:811–823 (1990).

Sanchez et al., "The efficiency and timing of plasmid DNA replication in Xenopus eggs: correlations to the extent of prior chromating assembly," Journal of Cell Science 103:907–918 (1992).

Wangh et al., "Injection of Xenopus eggs before activation, achieved by control of extracellular factors, improves plasmid DNA replication after activation," Journal of Cell Science 93: 1–8 (1989).

Newport et al., "Disassembly of the Nucleus in Mitotic Extracts: Membrane Visicularization, Lamin Disassembly, and Chromosome Condensation Are Independent Processes," Cell 48:219–230 (1987).

Brown et al., "In vitro, activation of human sperm nuclei using *Xenopus laevis* egg extract" Abstracts of Papers Presented at the Twenty–fourth Annual Meeting: The American Society for Cell Biology 99: 396a (1984).

Brown et al., "Partial Purification of *Xenopus Laevis* Egg Extract Factors) that Induce Swelling In Permeabliized Human Sperm," J. Exp. Zool. 258:263–272 (1991).

Brown et al., "Use of *Xenopus Laevis* Frog Egg Extract In Diagnosing Human Male Unexplained Infertility," Yale J. Biol. Med. 65:29–38 (1992).

Coppock et al., "Replication of Xenopus Erythrocyte Nuclei In A Homologous Egg Extract Requires Prior Proteolytic Treatment," Development Biology 131:102–110 (1989).

Dawson et al., "Data For Biochemical Research," Second Edition, Oxford University Press, Oxford, pp. 388–389 (1969).

Gordon et al., Exp. Cell Res. 157:409 (1985).

Graham, "The Regulation of DNA Synthesis And Mitosis In Multinucleate Frog Eggs," J. Cell Sci. 1:363–374 (1966).

Griveau et al, "Decondensation of Human Sperm Nuclei And HP1 Protamine Degradation From Normospermia And Asthenospermia In Xenopus Egg Extracts," Arch. Androl. 29:127–136 (1992).

Jackson "The Future In Prenatal Diagnosis," Seminars in Perinatology 15:49–51 (1991).

Leno et al., "The Nuclear Membrane Determines The Timing of DNA Replication In Xenopus Egg Extracts," J. Cell Biology vol. 112 No. 4 pp. 557–566 (1991).

Lohka et al., "Formation In Vitro of Sperm Pronuclei And Mitotic Chromosomes Induced by Amphibian Ooplasmic Components," Science 220:719–721 (1983).

Masui, "Hormonal And Cytoplasmic Control of the Maturation of Frog Oocytes," Ontogenez vol. 3 No. 6 pp. 574–587 (1972).

Masui et al., "Roles of Ca Ions And Ooplasmic Factors In The Resumption of Metaphase–Arrested Meiosis in Rana Pipiens Oocytes," Symp. Soc. Exp. Biol. 38:45–66 (1984).

Meyerhof et al., "Chromosome Condensation Activity In Rana Pipiens Eggs Matured In Vivo And In Blastomeres Arrested By Cytostatic Factor (CSF)," Exp. Cell Res. 123:345–353 (1979).

Montag et al., "In Vitro Decondensation of Mammalian Sperm and Subsequent Formation of Pronuclei–Like Structures For Micromanipulation," Mol. Reprod. Devel. 33:338–346 (1992).

Ohsumi et al., "Development of Pronuclei From Human Spermatozoa Injected Microsurgically Into Frog (Xenopus) Eggs," J. Exp. Zool. 237:319–325 (1986).

Ohsumi et al., "Human Sperm Nuclei Can Transform Into Condensed Chromosomes In Xenopus Egg Extracts," Gamete Res. 20:1–9 (1988).

Riabova et al., "A Contribution To The Chronology of Embryogenesis In The Common Frog," Ontogenez 15:93–97 (1984).

Roberts, FISHing Cuts The Angst In Amniocentesis, Science 254:378–379 (1991).

Zirkin et al., "In Vitro And In Vivo Studies of Mammalian Sperm Nuclear Decondensation," Gamete Research 11:349–365 (1985).

Adachi et al., "Identification of Nuclear Pre–Replication Centers Poised For DNA Synthesis In Xenopus Egg Extracts: Immunolocalization Study of Replication Protein A," J.Cell Biology vol. 119 No. 1 pp. 1–15 (1992).

Almouzni et al., "Xenopus Egg Extracts: A Model System For Chromatin Replication," Biochimica et Biophysica Acta, 951:443–450 (1988).

Almouzni et al., "Assembly of Spaced Chromatin Promoted By DNA Synthesis In Extracts From Xenopus Eggs," The EMBO Journal vol. 7 No. 3 pp. 665–672 (1988).

Almouzni et al., "Competition Between Transcription Complex Assembly And Chromatin Assembly On Replicating DNA," EMBO Journal vol. 9 No. 2 pp. 573–582 (1990).

Almouzni et al., "Nuclear Assembly, Structure, and Function: The Use of Xenopus In Vitro Systems," Exp. Cell Res. 205:1–15 (1993).

Blow et al., "Initiation of DNA Replication In Nuclei And purified DNA By A Cell–Free Extract of Xenopus Eggs," Cell 47:577–587 (1986).

Blow et al., "Nuclei Act As Independent And Integrated Units of Replication in A Xenopus Cell–Free DNA Replication System," EMBO Journal vol. 6 No. 7 pp. 1997–2002 (1987).

Blow et al., "A Role For The Nuclear Envelope In Controlling DNA Replication Within The Cell Cycle," Nature vol. 332 No. 7 pp. 546–548 (1988).

Blow et al., "Replication of Purified DNA In Xenopus Egg Extracts is Dependent on Nuclear Assembly," J. Cell Science 95:383–391 (1990).

Blow et al., "A CDC2–Like Protein Is Involved In The Initiation of DNA Replication In Xenopus Egg Extracts," Cell 62:855–862 (1990).

Blow, "Preventing Re–Replication of DNA In A Single Cell Cycle: Evidence For A Replication Licensing Factor," J. Cell Biology vol. 122 No. 5 pp. 993–1002 (1993).

Coverley et al., "Reversible Effects of Nuclear Membrane Permeabilization on DNA Replication; Evidence For A Positive Licensing Factor," J. Cell Biology vol. 122 No. 5 pp. 985–992 (1993).

Coverly et al., "Regulation of Eukaryotic DNA Replication," Annu. Rev. Biochem. 63:745–76 (1994).

Cox et al., "Extracts From Eggs And Oocytes of *Xenopus Laevis* Differ In their Capacities For Nuclear Assembly And DNA Replication," J. Cell Science 97:177–184 (1990).

Cox, "DNA Replication In Cell–Free Extracts From Xenopus Eggs Is Prevented By Disrupting Nuclear Envelope Function," J. Cell Science 101:43–53 (1992).

Hirano et al., "Topoisomerase II Does Not Play A Scaffolding Role In The Organization of Mitotic Chromosomes Assembled In Xenopus Egg Extracts," J. Cell Biology vol. 120 No. 3 pp. 601–612 (1993).

Hutchinson et al., "Periodic DNA Synthesis In Cell–Free Extracts of Xenopus Eggs," EMBO Journal 6:2003–2010 (1987).

Hutchinson et al., "The Control of DNA Replication In A Cell–Free Extract That Recapitulates A Basis Cell Cycle In Vitro," Development 103:553–566 (1998).

Hutchison et al., "DNA Replication And Cell Cycle Control In Xenopus Egg Extracts," J. Cell Sci. Suppl. 12:197–212 (1989).

Hutchison et al., "Changes In the Nuclear Distribution of DNA Polymerase Alpha And PCNA/Cyclin During The Progress of The Cell Cycle, In A Cell–Free Extract of Xenopus Eggs," J. Cell Sci. 93:605–613 (1989).

Hyrien et al., "Plasmid Replication In Xenopus Eggs and Egg Extracts: A 2D Gell Electrophoretic Analysis," Nucleic Acids Research vol. 20 No. 7 pp. 1463–1469 (1992).

Hyrien et al., "Chromosomal Replication Initiates And Terminates At Random Sequences But At Regular Intervals In The Ribosomal DNA of Xenopus Early Embryos," EMBO Journal vol. 12 No. 12 pp. 4511–4520 (1993).

Kornbluth et al., "In Vitro Cell Cycle Arrest Induced by Using Artificial DNA Templates," Molecular and Cellular Biology vol. 12 No. 7 pp. 3216–3223 (1992).

Leno et al., "The Nuclear Membrane Prevents Replication of Human G2 Nuclei But Not G1 Nuclei In Xenopus Egg Extract," Cell 69:151–158 (1992).

* cited by examiner

PRODUCT AND METHOD FOR SWELLING A CELL NUCLEUS WITHOUT DNA REPLICATION

RELATED APPLICATION

This application is a continuation of U.S. application Ser. No. 09/226,766, filed Jan. 6, 1999, pending; which is a continuation of U.S. application Ser. No. 09/050,380, filed Mar. 30, 1998, now U.S. Pat. No. 6,245,567; which is a continuation of U.S. application Ser. No. 08/455,981, filed May 31, 1995, now U.S. Pat. No. 5,773,217; which is a division of U.S. application Ser. No. 08/190,771, filed Feb. 1, 1994, now U.S. Pat. No. 5,651,992; which is a continuation-in-part of U.S. application Ser. No. 08/013,039, filed Feb. 3, 1993, now U.S. Pat. No. 5,480,772.

FIELD ON THE INVENTION

This invention concerns products, methods and apparatus for analysis of non-dividing mammalian cell nuclei, such as human fetal cell nuclei and mammalian sperm cell nuclei.

BACKGROUND OF THE INVENTION

Jackson, *Seminars in Perinatology* 15:49 (1991), describes various procedures for prenatal diagnosis, including procedures to diagnose diseases. These procedures involve analysis of the DNA present in early embryonic stages. Specifically, Jackson mentions the use of a polymerase chain reaction to amplify genes, and the possibility of testing oocytes by polar body assay. According to Jackson:

"There are other conceivable embryo biopsy approaches for prenatal diagnosis. The trophectoderm may be obtained at later, multicellular embryonic stages when more cells might be obtained and induced to replicate in tissue culture . . . Another approach to early prenatal diagnosis is the recovery of fetal cells in the maternal circulation. This tantalizing possibility for a non-invasive method has been pursued for several years by groups in both the United States and the United Kingdom. Both groups originally sought placental immunologic markers for identification and recovery of these cells. Several trophoblast antibodies were developed, some of which appeared to have relative specificity for the fetal cell. After sporadic reports of success, recent articles appear to indicate that these markers are insufficiently specific and actually are attached to maternal cells frequently enough to make this approach unworkable to date."

Bianchi et al., *Proc. Natl. Acad. Sci. USA* 87: 3279 (1990), describe isolating fetal nucleated erythrocytes in maternal blood using a monoclonal antibody against the transferrin receptor. They state that they "were successful in detecting the Y chromosomal sequence in 75% of male-bearing pregnancies, demonstrating that it is possible to isolate fetal gene sequences from cells in maternal blood."

According to Roberts, *Science* 18:378 (1991), two procedures available for prenatal screening are chorionic villus sampling (CVS) and amniocentesis. Both these procedures have problems involving waiting time and risk of miscarriage, "estimated at 1% to 2% for CVS and 0.5% for amniocentesis." *Supra*. Roberts also points out a procedure for analyzing nuclear DNA directly when cells are in interphase.

Lohka and Masui, *Science* 220:719 (1983), describe inducing the formation of a nuclear envelope in demembraned sperm of *Xenopus laevis* using a cell-free preparation from the cytoplasm of activated eggs of *Rana pipiens.*

Leno and Laskey, *J. Cell Biology* 112:557, (1991), performed experiments using erythrocytes from adult chickens. According to Leno:

"Coppock et al. (1989) [*Supra*] have reported that a pretreatment with trypsin was required for nuclear decondensation and DNA replication of *Xenopus* erythrocyte nuclei in egg extract. Trypsin pretreatment was not required for nuclear decondensation and DNA replication in our extracts."

Gordon et al., *Experimental Cell Research* 157:409 (1985), describe "a system for the activation of human sperm using cell-free extracts from *Xenopus laevis* eggs." Similarly, an abstract, by Brown et al., *J. Cell Biology* 99:396a (1984), indicate that nuclear changes which occur during the early phases of fertilization can be stimulated by injecting isolated sperm nuclei into heterologous recipient eggs, or by incubating frog sperm nuclei in the presence of cell-free extracts from frog eggs. They state that they found human sperm can be activated in vitro using *Xenopus laevis* frog egg extract to stimulate the early events of nuclear activation, including chromatin decondensation, nuclear enlargement and DNA synthesis.

SUMMARY OF THE INVENTION

The present invention concerns products and methods useful for causing non-dividing nuclei to activate (e.g., go through one or more steps of nuclear activation). The featured products and methods are particularly useful for activating human fetal cell nuclei and mammalian sperm cell nuclei. "Activation" of a non-dividing cell nucleus refers to one or more of the following activities: nuclear swelling, nucleic acid replication, and nuclear entrance into mitosis thereby producing metaphase chromosomes (arrested metaphase chromosomes or replicating chromosomes). Complete activation refers to activation wherein all of the activities occur.

Nucleic acids can be analyzed at the different stages of activation, brought about by the present invention, to obtain useful information such as information about nucleic acid structure, sequences, number of copies of a nucleic acid sequence, and nuclear location of a nucleic acid. Analysis of nucleic acids can be carried out using techniques known in the art such as in situ hybridization and karyotype analysis of metaphase chromosomes.

One particular advantage of the present invention is its use in prenatal diagnosis. Activation of fetal cell nuclei can be used to facilitate prenatal diagnosis of various human conditions. Nuclei from of all types of human fetal cells including blood cells (such as red cells, white cells and other circulating cells of the fetus), as well as other types of fetal cells such as cells found in the amniotic fluid, or cells derived from the placenta (such as trophoblasts or syncytial trophoblasts), can be activated using the described products and methods. Preferably, the fetal cells to be activated are recovered from the blood or tissue of a pregnant woman rather than directly from the fetus or placenta, thereby decreasing the likelihood of discomfort or harm to the fetus and/or mother by the diagnosis procedure.

"Activation activity" refers to the ability of an agent to bring about nuclear activation. Examples of agents which bring about nuclear activation include a non-activated cytostatic factor (CSF) extract and activating egg extract. Enhancement of activation activity refers to an increase in the activation activity which is brought about by an agent which causes nuclear activation. Examples of agents which enhance nuclear activation caused by an activating agent include CSF extract, purified components thereof, and proteases.

Activation activity can be measured using techniques known in the art. Such techniques include microscopic visualization of swollen nuclei, incorporation of labelled nucleic acid precursors into newly synthesized nucleic acid, microscopic visualization of metaphase chromosomes, and in situ hybridization.

The featured methods include pretreating a non-dividing human nucleus to enhance its ability to activate, bringing about complete or partial nuclear activation, and both bringing about and analyzing such nuclear activation on a microchamber microscope slide. Other useful methods disclosed include preparing products such as an activating egg extract, a CSF extract, and a modified CSF extract; the use of a protease pretreatment step in the activation of sperm; an activation assay; a retroviral integration assay; and a procedure for cloning whole animals using activated nuclei.

The featured products including activating egg extract, CSF extract, kits containing these extracts, and a microchamber microscope slide useful in analyzing nuclear activation, are also claimed as part of the present invention.

The nucleus of a non-dividing fetal cell or a sperm cell is normally small, has condensed chromatin, and does not replicate or divide. Specific nucleic acid sequences in the nucleus of these cells can be stained by fluorescent in situ hybridization methods if the target nucleic acid sequence is accessible to the probe. However, the small size of the nucleus can affect the accessibility of particular nucleic acid sequences and the amount of information obtained from successful hybridization. Moreover, hybridization signals successfully obtained are limited in spacial resolution by the size of the nucleus. As a result, obtaining a reliable fluorescent signal can be difficult and the information obtained by fluorescent staining generally indicates only the presence or absence of accessible specific sequences, and possibly the number of such sequences per nucleus.

In the featured methods, the present invention brings about one or more stages of nuclear activation: nuclear swelling, chromatin decondensation, DNA replication, and formation of metaphase chromosomes. Genetic information can be obtained from each of these stages, which are characterized by changes in nuclear structure and function. Useful information obtained from these stages of activation include facilitating the visualization of a particular chromosomal region using a probe by increasing the spacial resolution during swelling thereby increasing accessibility of the chromosomal region to the probe; detecting the number of a particular type of chromosome initially present by determining the increased number of the particular chromosome brought about by replication; and visualizing chromosomal morphology by staining metaphase chromosomes, including the presence of one or more sequences at specific locations within chromosomes.

Thus, in the first aspect, the invention features a method for causing a nucleus from a human fetal cell to activate. Activation is brought about by contacting a pretreated or, preferably, a further pretreated nucleus, with activating egg extract.

The present invention can be used to study fetal cell nuclei acid isolated by different procedures. For example, fetal cells can be obtained from circulating maternal blood, or by techniques such as amniocentesis or chorionic biopsy. Preferably, the fetal cell is obtained in a non-invasive manner (e.g., without disturbing the womb). Fetal cells such as erythrocytes and leukocytes cross the placenta and circulate transiently in maternal blood. Furthermore, trophoblasts which form the outermost placenta layer can pinch off and circulate in maternal blood. Trophoblasts typically end up trapped in the maternal lung capillary network.

Nuclear isolation and pretreatment is preferably carried out using mild conditions. Mild conditions are those which allows for nuclear isolation and pretreatment while causing the minimal amount of protein and nucleic acid damage. Using mild conditions helps maintain the integrity of the nucleic acid thereby decreasing artifacts during subsequent staining, and prevents premature protease activation thereby allowing subsequent protease treatment to occur under controlled conditions chosen to optimize such treatment.

Preferably, nuclear isolation and pretreatment to release a nucleus from its surrounding cytoskeleton thereby forming a pretreated nucleus is carried out in two steps; (1) membrane permeabilization, and (2) separation or alteration (e.g., denaturation or degradation) of cytoskeletal proteins and nuclear matrix proteins. These steps may be carried out simultaneously or separately. Formation of a pretreated nucleus is preferably carried out under conditions minimizing nucleic acid damage and damage to histones.

Membrane permeabilization, opens up the membrane thereby facilitating subsequent nuclear treatment. Different techniques may be used for membrane permeabilization including hypotonic shock, shearing and detergent. Preferably a non-ionic detergent is used to permeabilize the plasma and nuclear membranes. More preferably, lysolecithin is used as the non-ionic detergent.

Different procedures can be use to separate, denature, and degrade the cytoskeletal proteins surrounding the nucleus and nuclear matrix proteins within the nucleus. These procedures include the use of a thiol reducing agent to denature nuclear protein, using controlled salt extraction to selectively remove cytoskeletal and nuclear matrix proteins, and using controlled poly-anionic treatment to facilitate separation of negatively charged nucleic acid from the positively charged nuclear proteins. Separation conditions should be chosen to ensure a minimal amount of damage to nucleic acids, histones, and non-cytoskeletal proteins. Preferably, a protease is used under mild conditions to remove cytoskeletal proteins surrounding the nucleus. More preferably, trypsin is used as the protease. In the most preferred embodiment, pretreatment is achieved using trypsin and lysolecithin.

Activating egg extracts are used to bring about nuclear activation. Activating egg extracts contain material, such as precursors, protein(s), nuclear envelope vesicles and mRNA, which support nuclear activation. An egg can be chemically, physically, or electrically induced to produce material which brings about nuclear activation. Eggs can be induced using a calcium ionophore as described below. The induced egg continues in its cell cycle. It appears that when an egg is at the point in the cell cycle just prior to the S-phase, the egg cytoplasm is most active in supporting activation. As the egg proceeds into and past the S-phase, it appears to produce material inhibitory to activation.

Preferably activating egg extracts are prepared from *Xenopus* eggs. More preferably activating egg extract are prepared from eggs having an elevated DNA synthesis activation activity. Activating egg extract prepared from *Xenopus* eggs induced for 10 minutes at 20° C. contain approximately 59% of the optimal DNA synthesis activation activity of *Xenopus* eggs induced for 25 minutes at 20° C. At about 25–30 minutes at 20° C. the *Xenopus* eggs are at highest (optimal), or peak, DNA synthesis activation activity. *Xenopus* eggs induced for 40 minutes at 20° C. appear to have a lower DNA synthesis activation activity than the peak activation activity. Thus, the present invention discloses the use of induced eggs having an elevated DNA synthesis activation activity of 70% or greater of the peak activation activity.

Activating extracts prepared from *Xenopus* eggs induced for 10 minutes or less at 20° C. produce a lower rate of DNA replication in treated nuclei. However, activating extract prepared from *Xenopus* eggs induced for 10 minutes at 20° C. appear to produce equivalent or greater nuclear swelling in treated nuclei than extracts prepared from *Xenopus* eggs induced for more than 10 minutes at 20° C.

More preferably activating egg extract is prepared from a number of eggs (e.g., 1,000 to 10,000), most or all of which have an elevated or peak DNA synthesis activation activity. Obtaining a large number of eggs having a peak or elevated DNA synthesis activation activity is preferably achieved using hardened eggs which have been synchronously induced. Hardened eggs are prepared by hardening the vitelline envelope surrounding the egg (described in detail below). Hardened eggs are less likely to spontaneously activate than soft non-hardened eggs.

Thus, by using hardened eggs a large number of eggs can be collected and induced at the same time (synchronously induced). A given number of eggs synchronously induced should all be at or near the same point in their cell cycle at a given later time. A large number of eggs having an elevated DNA synthesis activation activity can be obtained by inducing the eggs at one time, and preparing the activating egg extract from all the eggs at a second later time. Preferably the activating egg extract is stored frozen. Freezing the extract allows a large amount of extract to be prepared at one time and used at different later times.

Various supplements to activating egg extract have been found to increase the activation activity of the activating egg extract. These supplements include cell cycle regulatory proteins, cell cycle inhibitors, cAMP (preferably, between 0.1 and 1.0 mM, most preferably at 0.3 mM), and phosphodiesterase inhibitors (preferably caffeine, more preferably caffeine at a concentration between 0.1 and 10.0 mM, most preferably caffeine at a concentration of 1 mM).

In another preferred embodiment activation occurs under nuclear non-duplication conditions wherein the nucleus swells, replicates DNA, forms metaphase chromosomes and prepares to divide (i.e., enters mitosis), but segregation of sister chromatids is prevented by inhibiting spindle formation. The inhibition of spindle formation prevents the division of the cell nucleus and the resulting separation of metaphase chromosomes.

Thus, under non-duplication conditions metaphase chromosomes are detectable for a longer time period and are provided in a "spread pattern." A "spread pattern" refers to the orientation of different chromosomes with respect to each other. Drugs such as nocodazole, colchine, or colcemid can be used to inhibit spindle formation. Preferably nuclear non-duplication conditions is achieved by adding nocodazole to the activating egg extract. More preferably, nocodazole is in an amount which will not inhibit DNA replication (e.g., less than 5 $\mu$g/ml).

In other preferred embodiments, prior to being treated with the activating egg extract, the pretreated nuclei are further pretreated by contact with a CSF extract, or a purified component of the CSF extract including a purified kinase or a purified phosphatase. By "purified" is meant the component is more concentrated (e.g., has a higher specific acitivity) than when present in a CSF extract. The desired purified kinase or phosphatase can be obtained by purifying the enzymes from CSF fractions and assaying for activation activity. Further pretreatment with CSF is preferably carried out under conditions not resulting in nucleus activation. Premature activation occurring under non-controlled conditions decreases the ability of CSF extracts to enhance activation because activation is occurring in CSF extract under non-optimized conditions. Another disadvantage of premature activation is that it produces a pool of nuclei activated at different times, which is more difficult to examine than nuclei activated at the same time.

CSF extracts can be used to increase nuclear activation upon subsequent contact with an activating agent. CSF extracts can be prepared from non-induced eggs (i.e., eggs arrested in meiotic metaphase II or activated eggs that have been arrested in mitotic metaphase). These extracts contain factors which aid in nuclear activation, such as CSF and mitosis promoting factor (MPF). MPF may help bring about activation and visualization of chromosome by stimulating chromosome condensation and inhibiting spindle assembly.

A preferred source of CSF extracts is *Xenopus* eggs. Isolation of CSF extract from *Xenopus* eggs is facilitated using "hardened eggs" which do not spontaneously induce. Preferably, the CSF extract is stored frozen. Freezing the extract allows a large amount of extract to be prepared at one time and used at different later times.

CSF extract is preferably supplemented with reagents such as β-glycerol phosphate, creatine phosphate, phosphocreatine kinase, and $Ca^{2+}$ in amounts which improves activation of nuclei in activating extract, without causing the start of the cell cycle prior to contact with activation egg extract. Preferably, the CSF extract contains $Ca^{2+}$ in an amount which leads to an increase in the level of histone kinase or MPF activity without initiating the cell cycle. The use of $Ca^{2+}$ to supplement CSF extract is particular advantageous if the CSF extract is frozen before use. The $Ca^{2+}$ may be added before freezing or after thawing.

$Ca^{2+}$ is a cofactor for calmodulin activated protein kinases and may increase CSF activity by increasing the level of phosphorylated topoisomerase II activity. Topoisomerase II is a scaffold protein which aids in chromosome decondensation and condensation possibly by anchoring chromatin loop domains. Wood and Earnshaw, *J. Cell Biology* 111:2839 (1990). $Ca^{2+}$ also appears to increase the histone kinase level, which we have used as one measure of MPF activity.

As would be appreciated by one skilled in the art, the optimal amount of $Ca^{2+}$ added to a CSF extract varies depending upon the presence of a $Ca^{2+}$ chelator. The $Ca^{2+}$ concentration is preferably equal to or greater than 100 $\mu$M; more preferably the $Ca^{2+}$ concentration is between 100 $\mu$M and 400 $\mu$M. These preferred concentrations were determined using a CSF extract supplemented with 1 mM ethylene glycol-bis(β-aminoethyl ether)N,N,N'N'-tetraacetic acid (EGTA).

In another preferred embodiment, nuclei are activated under non-synthesis conditions which inhibit nucleic acid synthesis. As a result, the nucleus swells with or without formation of a nuclear envelope but does not replicate DNA or enter mitosis. The resulting increased spacial resolution brought about by nuclear swelling facilitates the use of nucleic acid probes by making regions of nucleic acid more accessible. Non-synthesis conditions, which nevertheless permit nuclear swelling may be achieved by the addition of reagents such as aphidicolin (e.g., 50–100 $\mu$g/ml), 6-dimethylaminopurine (e.g., at 5 mM), leupeptin (e.g., at 5 $\mu$g/ml) dideoxycytidine triphosphate (e.g., 0.1 mM) or dideoxythymidine triphosphate (e.g., 0.1 mM) to an activated egg extract, or to CSF extract which is then contacted with an activated egg extract.

In another aspect, a non-dividing human nucleus is further pretreated for subsequent activation by contact with a purified protein kinase or a purified phosphatase which is present in a CSF extract. The purified protein kinase or purified phosphatase is in a purer form (e.g., more concentrated or more active) than that found in a CSF extract.

In a third aspect, the invention features a method for activating a non-dividing human nucleus by further pretreating the non-dividing human nucleus in CSF extract, prepared from hardened eggs, and then contacting these further pretreated nuclei with an activating egg extract prepared from synchronously induced hardened eggs.

In preferred embodiments the CSF extract is frozen before use and the activating egg extract is frozen before use.

In other preferred embodiments, pretreated nuclei undergo further pretreatment in CSF extract involving a warm-then-cold incubation regime. Both the warm and cold steps increase activation of nuclei upon subsequent contact with activating extract. Preferably, incubation is carried out at about 25° C. for at least 30 minutes followed by incubation at about 4° C. for at least 30 minutes. Less preferred, but still an effective incubation, is a warm regime at about 25° C. for at least 30 minutes.

In other preferred embodiments, thawed CSF extract is supplemented with $Ca^{2+}$ in an amount which does not start the cell cycle but improves nuclei activation. The $Ca^{2+}$ should be in an amount which leads to an increase in the level of histone kinase or MPF without initiating the cell cycle.

In another aspect, methods are described for preparing an activating egg extract, from hardened eggs, which can cause non-dividing human nuclei cells to activate. The activating egg extracts are prepared from hardened eggs which have been synchronously induced such that the activating egg extract is prepared from eggs having an elevated DNA synthesis activation activity. Preferably synchronous induction is carried out using eukaryotic cells, more preferably amphibian, yeast, human, echinoderm, mollusc, or fish, or chicken cells are used; more preferably Xenopus eggs are used; even more preferably Xenopus eggs induced for more than 10 minutes are used; most preferably Xenopus eggs are induced for 25–30 minutes at 20° C.

In another aspect a method for inducing swelling in non-dividing nuclei is described. The method can be used to induce swelling in the absence of an activating extract and in the absence of DNA synthesis. In particular, CSF extract is supplemented with a protein kinase inhibitor and/or an aqueous solution.

In another aspect, a method for chromosome formation without DNA replication is described. The method involves using a CSF extract supplemented with a cyclin such as cyclin-Δ90 in an amount sufficient to enhance nuclear envelope breakdown and nuclear chromosome formation. The cyclin is thought to act by raising the level of MPF activity in a CSF extract.

In another aspect, a method for activating a mammalian sperm cell nucleus is described. The method involves the steps of: (a) pretreating a sperm cell, using a membrane permeabilizer, a protease, and a thiol reducing agent to form a pretreated sperm cell; and (b) activating the pretreated sperm cell. The method can be used to study sperm from different mammals. Such studies can be carried out, for example, to determination whether the sperm contains a particular gene or nucleic acid sequence which can be passed on during fertilization.

In another aspect, activation assays are described. These assays can be used to measure different stages of activation. A basic assay comprises isolating a nucleus, pretreating the nucleus, further pretreating the nucleus, contacting the further pretreated nucleus with an activating egg extract and measuring activation activity. Measurement of activation activity can be carried out using standard techniques such as incorporation of labelled nucleotides into newly synthesized nucleic acid and microscopic visualization of nuclear swelling and metaphase chromosome formation.

Other activation assays are performed by altering one or more of the steps of the basic assay. For instance, to assay for important factors in CSF extract, rather than using whole CSF extracts, fractions of the extract can be used. These fractions are obtained using standard purification techniques. Similarly, different activating egg extract fractions can be studied.

In a preferred embodiment, a sperm activation assay, particularly useful to study human male fertility, is described. Uses of the sperm activation assay include, determining the effect of handling sperm under different condition thereby obtaining optimal handling condition for subsequent in vitro fertilization, and testing the effect of possible male contraceptives on activation.

In other aspects viral integration assays involving the use of a cell nucleus or a pseudonucleus are described. Viral integration into a cell nucleus can be assayed as follows: pretreating a cell nucleus to separate the nucleus from its surrounding cytoskeleton; activating the pretreated nucleus and incubating with a viral integration complex containing viral nucleic acid; and measuring integration of viral nucleic acid into nucleic acid of the cell nucleus. The viral integration complex containing viral nucleic acid can be added at different times during nuclear pretreatment and activation.

The viral integration assay using a pseudonucleus involves: a) constructing a pseudonucleus from a defined DNA template; b) replicating the pseudonucleus; and c) incubating the pseudonucleus in the presence of a viral integration complex containing viral nucleic acid. This integration complex can be added at any time during pseudonucleus formation or replication. A pseudonucleus can be constructed, for example, by adding plasmid DNA to a CSF extract or an activating extract. The plasmid forms chromatin in the CSF extract but does not replicate until $Ca^{2+}$ (1–4 mM) is added. Activation of the extract containing the pseudonucleus leads to nuclear envelope formation around the chromatin template and causes the chromatin to replicate.

In another aspect, a product for further pretreatment of nuclei is described. The further pretreatment product comprises CSF with extract supplemented with $Ca^{2+}$. $Ca^{2+}$ is provided in an amount which increases nuclei activation upon subsequent contact with activating extract. Preferably, the CSF extract is also supplemented with β-glycerol phosphate, creatine phosphate, and phosphocreatine kinase, In preferred embodiments the CSF extract is frozen; the $Ca^{2+}$ concentration is equal to or greater than 100 μM; more preferably the $Ca^{2+}$ concentration is between 100 μM and 400 μM. These preferred embodiments were determined using a CSF extract supplemented with 1 mM EGTA.

In another aspect, a product for causing nuclear swelling is described. The product contains CSF extract supplemented with a protein kinase inhibitor and/or an aqueous solution.

In another aspect a product for causing chromosome formation without DNA replication is described. The product is made up of a CSF extract supplemented with a cyclin such as cyclin-Δ90 in an amount sufficient to bring about nuclear envelope breakdown and nuclear chromosome formation.

In another aspect, a product for causing a non-dividing nucleus to activate is described. The activating product comprises an activating egg extract prepared from an egg(s) having an elevated DNA synthesis activation activity.

In a preferred embodiment activating egg extract is prepared from *Xenopus* eggs synchronously induced for more than 10 minutes; preferably the *Xenopus* eggs are induced for 25 to 30 minutes at about 20° C.

In other preferred embodiments, the activating egg extract is modified by supplementation with cell cycle regulatory proteins, cell cycle inhibitors, cAMP (preferably, between 0.1 and 1.0 mM, most preferably at 0.3 mM), and phosphodiesterase inhibitors (preferably caffeine, more preferably caffeine at a concentration between 0.1 and 10.0 mM, most preferably caffeine at a concentration of 1 mM).

In another aspect, a kit is disclosed for activating a non-dividing nucleus. The kit is comprised of frozen activating egg extract prepared from an egg having an elevated DNA synthesis activation activity and frozen CSF extract.

In a preferred embodiment the CSF extract contains $Ca^{2+}$. In a most preferred embodiment the kit contains a microchamber microscope slide.

In another aspect, the invention features a microchamber microscope slide provided with an upper surface having a water-repellent material of a known thickness defining a microchamber on the upper surface. The microchamber is shaped to enhance flushing of the microchamber, and connected by at least one channel to a well on the upper surface.

In preferred embodiments, the microchamber is teardrop-shaped or pear-shaped; preferably two wells are provided at opposite ends of the microchamber connected by two separate channels to the microchamber; and the microchamber has a defined volume preferably between 5 and 50 μl, more preferably between 10 and 20 μl when a coverslip is placed over it. Fluid can be introduced into the microchamber by placing fluid in one well and allowing it to flow through the microchamber to the opposite well. The fluid is then removed from the opposite well. Removal may be achieved by pipetting away the fluid or by capillary action by placement of a filter paper within the well.

In other preferred embodiments, the water-repellent material is a tape or a coating on the upper surface of the slide, more preferably a TEFLON® coating, or a wax film (e.g., a PARAFILM®). In most preferred embodiments, the upper slide surface is treated to enhance cell growth compared to an untreated slide, the slide is provided in a sterile condition, and/or the slide is coated with an antibody able to specifically bind to a human fetal cell.

The advantages of the present invention include, but are not limited to, facilitating prenatal screening by optimizing conditions for nuclear activation, which causes the nucleus of a fetal cell to either swell, replicate nucleic acid, and/or form metaphase chromosomes. Important information regarding nucleic acid sequences or chromosome morphology can be readily obtained from these various stages of activation, for example by using DNA probes or visualizing the produced metaphase chromosomes. Because some fetal cells, such as trophoblasts, erythrocytes, and leukocytes can be obtained from a maternal source, an advantage of the invention is a non-invasive procedure to detect the presence of genetic defects in such cells.

Other features and advantages of the invention will be apparent from the following description of the preferred embodiments thereof, and from the claims.

DESCRIPTION OF THE PREFERRED EMBODIMENTS

The drawings will first briefly be described.
Drawings
FIG. 1 shows the effect on DNA replication of activated nuclei, of using frozen/thawed activating egg extracts supplemented with caffeine.

METHODS AND PRODUCTS

Figure 1:
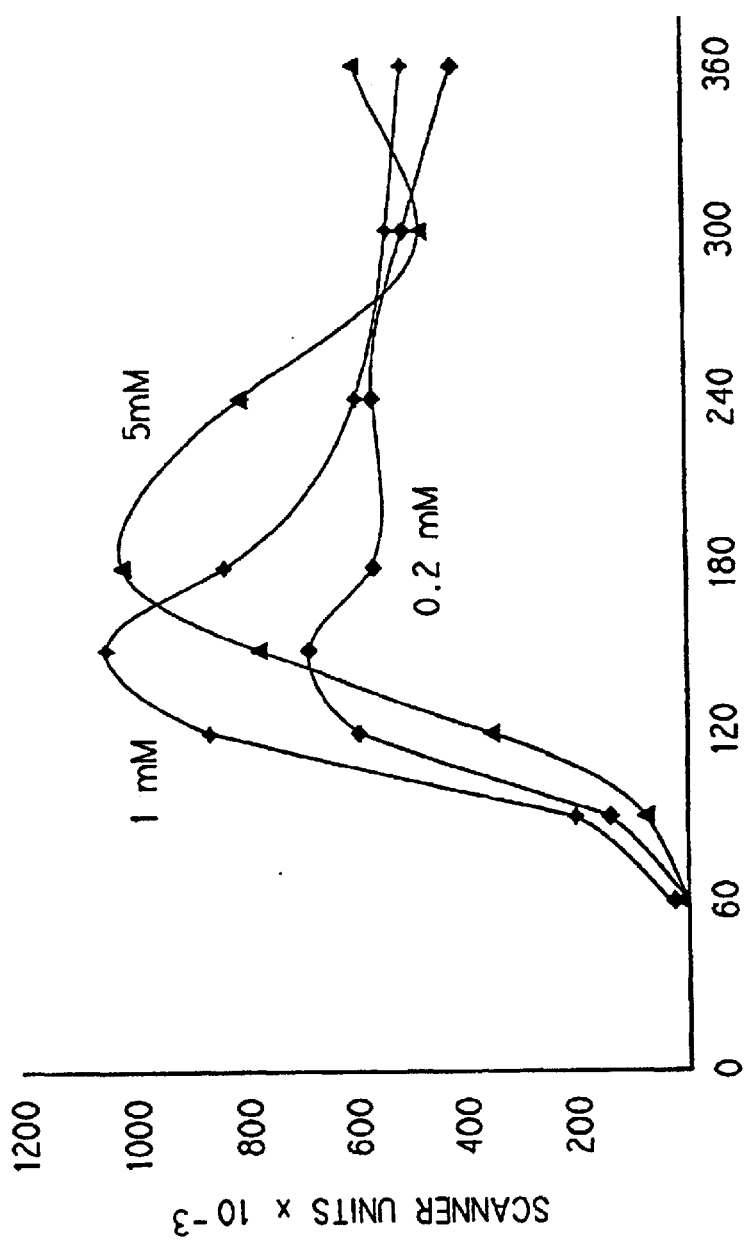

Methods for activating nuclei include those described by Coppock et al., *Developmental Biology* 131:102 (1989); Wangh, *J. Cell Science* 93:1 (1989); Wood and Earnshaw, *J. Cell Biology* 111:2839 (1990); Leno and Laskey, *J. Cell Biology* 112:557 (1991); Young, *Biology of Reproduction* 20:1001 (1979); Philpott et al., *Cell* 65:569 (1991); Shamu and Murray, *J. Cell Biology* 117:921 (1992); Adachi et al., *Cell* 64:137 (1991); Newport and Spann, *Cell* 48:219 (1987); and Henry Harris, in *CELL FUSION* 40–50 (Harvard University Press 1970).

DiBerardino et al., *Proc. Natl. Acad. Sci. USA* 83:8231 (1986), and Orr et al. *Proc. Natl. Acad. Sci. USA* 83:1369 (1986) describe nuclear transplantation experiments to activate *Rana pipiens* nuclei. DiBerardino was able to obtain tadpoles having a survival rate of up to a month, by transplanting differentiated somatic cells into enucleated eggs.

The present invention discloses methods and products useful in activating a non-dividing nucleus, and studying such activation. These methods and products are especially useful for analyzing a nucleus from non-dividing human fetal cells such as aminocytes, keratinocytes, trophoblasts, erythrocytes and leukocytes. However, the methods and products are also useful for activating the nuclei from other types of non-dividing human cells such as other types of non-dividing fetal cells and sperm, and non-dividing cells isolated from other mammals.

Preparing a nucleus for nuclear activation and bringing about nuclear activation is described in detail below as four different phases: (1) preparation of non-dividing human nuclei, (2) preparation of activating egg extracts from a source such as activated *Xenopus* eggs, (3) preparation of non-activated CSF extracts from a source such as non-activated *Xenopus* eggs, and (4) activation of non-dividing human nuclei.

Also described in detail below are modified CSF extracts which can bring about nuclear swelling in the absence of an activating egg extract; new procedures of pretreating a sperm cell to enhance its activation; a microchamber microscope slide which facilitates bringing about nuclei activation and analysis of nucleic acids in such cells; a kit for bringing about nuclear activation; an activation assay; and a procedure for cloning whole organisms from somatic cell nuclei.

The featured methods and products can be used to cause activation of a non-dividing human nucleus thereby inducing swelling, and/or DNA replication and/or the formation of metaphase chromosomes. The procedures provided herein regarding nuclei activation are generally based upon existing procedures used in other systems. However, several improvements over the existing systems are disclosed. Furthermore, existing procedures have not previously been used on human fetal cells nor was it known if they would produce useful results on such cells.

Examples are given to illustrate different aspects and embodiments of the present invention. It is to be understood that various different modifications are possible and are contemplated within the true spirit and scope of the appended claims. There is no intention, therefore, of limitations to the exact process or disclosure herein presented.

In particular, there is shown below the activation of a human fetal red blood cell nucleus using frozen/thawed activating egg extract without further pretreatment, under non-dividing conditions. The treated nuclei swelled significantly, replicated DNA, and then entered and arrested in the pre-mitotic state. Such nuclei are useful for prenatal diagnosis. Furthermore, the use of further pretreatment, should increase the rate and extent of nuclear swelling, decrease the time it takes for DNA synthesis to occur after activation, increase the rate and extent of DNA synthesis, and improve the efficiency with which metaphase chromosomes are formed.

I. Nuclear Activation (1) Preparation Of Nuclei

The present invention provides a method for activation non-dividing mammalian cell nuclei, preferably non-dividing human cell nuclei. Before being activated non-dividing human nuclei are isolated and pretreated. A preferred source of non-dividing human cells are fetal cells recovered from the blood of pregnant women such as trophoblasts, erythrocytes and leukocytes (such as granulocytes, neutrophils, basophiles and eosinophils). Isolating these cells does not require penetration of the womb. The present invention is also useful for analyzing other types of non-dividing human cell nuclei, including non-dividing keratinocytes (e.g., those isolated from amniotic fluid), aminocytes, and sperm cells, or similar cells obtained from mammals other than humans.

Non-dividing fetal cells can be recovered from maternal blood supply using techniques such as antibody staining followed by cell sorting. (For example, see Bianchi entitled Non-Invasive Method For Isolation and Detection of Fetal DNA" PCT/US90/06623, hereby incorporated by reference herein). Antibody cell sorting techniques separate fetal and maternal cells based on the presence of different antigens on fetal and maternal cells. The antigen can be differentiated by suitable antibodies. Such antibodies which can be obtained by one skilled in art include HLe-1 which recognizes an antigen present on mature human leukocytes, such as granulocytes, and very immature erythrocyte precursor but not nucleated cells, and antibodies to the transferrin receptor. (E.g., see Bianchi, supra PCT/US90/06623.) Procedures using antibodies can be carried out by contacting a sample containing fetal and maternal blood with a labeled antibody recognizing either fetal cells or maternal cells. The antibody labeled cell can be sorted using standard techniques including flow cytometry, immunomagnetic beads and cell panning.

Non-dividing human cells should be isolated under mild conditions designed to prevent activation of extracellular proteases (for instance those of the plasma), intracellular proteases, or nucleases, as well as to prevent mechanical damage to cell structures. Inadvertent protease or nuclease activation during nuclear isolation could result in damaging both the genetic material of the cell and the protein structures within or around the nucleic acid. Possible nucleic acid damage includes, nucleic acid degradation, and damage to the structural state (e.g., supercoiling). One advantage of keeping the protein structure intact, is maintaining the cytoskeletal protein so it can be subsequently separated from nucleic acid under mild conditions minimizing damage to histones and non-skeletal proteins.

Preferably, solutions used to isolate cells contain protease inhibitor. Solutions used to isolate cells such as HBSS and NIB solutions can be supplemented with protease inhibitors as follows: 0.1 mg/ml heparin, 0.1 mM TPCK (N-tosyl-L-phenylalanine chloromethyl ketone), 0.1 mM TLCK (Nα-p-tosyl-L-lysine chloromethyl ketone), 0.05 mM PMSF (phenylmethylsulfonyl fluoride), 5 µg/ml leupeptin, or 31.25 mM $Na_2S_2O_5$.

After cell purification, the cell nucleus is preferably isolated and pretreated under mild conditions. Nuclear pretreatment is preferably comprised of two steps, which may be carried out simultaneously or separately; (1) membrane permeabilization, and (2) separation or alteration (e.g., denaturation and degradation) of cytoskeletal proteins and nuclear matrix proteins. Treatment should be carried out to minimize the damage to nucleic acid within the nucleus.

The separation or alteration of certain protein appears to be a necessary step for activation. In *Xenopus* erythrocytes, for instance, proteolytic digestion of cytoskeletal proteins, such as vimentin, appears to be a necessary step for subsequent nuclear activation. Coppock et al. *Developmental Biology* 131:102 (1989). The pretreatment should prepare the nucleus for subsequent activation rather than cause activation.

Desired conditions for plasma membrane permeabilization include mild detergent treatment, mild protease treatment, mild shearing, and mild hypotonic shock. Mild conditions are those conditions able to permeabilize the plasma membrane while creating the least amount of damage to the nuclear DNA and proteins. Permeabilization can be detected using trypan blue. Trypan blue is a dye which cannot enter intact cells. The entrance of trypan blue into a cell indicates permeabilization. Protein degradation due to inadvertent protease activation can be determined using polyacrylamide gel electrophoresis to look for protein degradation products. The intactness of nuclear nucleic acids can be established by using agarose gel electrophoresis to determine the presence of nucleic acid degradation products.

Possible pretreatments for separation or alteration of cytoskeletal proteins and nuclear matrix proteins include the following:

(a) Treatment with one or more thiol reducing agent such as 10 mM dithiothreitol for a limited time, at a controlled temperature and pH, to denature cytoskeletal protein;

(b) Controlled salt extraction, such as by washing in buffers supplemented with increasing amounts of NaCl or KCl in the range of 0.025 to 1.0 M, to selectively remove cytoskeletal proteins and proteins bound to DNA;

(c) Controlled poly-anion treatment, such as heparin at 0.01–1.0 mg/ml or penta sodium tripolyphosphate at 70 mM, in 10 mM borate buffer (TPP) at pH 9.0, to selectively remove positively charged cytoskeletal protein;

(d) Degradation of cytoskeletal proteins using a protease.

The extent of protein and DNA damage can be measured as described above. Preferably, nuclear isolation and pretreatment are both accomplished at the same time using mild concentrations of lysolecithin (e.g., 40 µg/ml) and protease (e.g., 0.3 µg/ml trypsin), such that a minimal amount of damage to non-cytoskeletal proteins, histones, and nucleic acid occurs. The minimum time and temperature required for detergent and protease treatment should be used. In the case of red blood cells this is about 10 minutes at 25° C., using 0.3 µg/ml of trypsin and 40 µg/ml of lysolecithin. As would be appreciated by one skill, the preferred time and temperature will change as the concentration of the reagents change.

Controlled treatment with ion-selective chelating agents may also be performed as an additional pretreatment. Suitable ion-selective chelating agents include EGTA which can chelate $Ca^{2+}$, EDTA which can chelate $Ca^{2+}$ and $Mg^{2+}$, and mimosine which can chelate of $Cu^{2+}$, $Al^{3+}$, and $Fe^{3+}$. These ions stabilize higher order chromatin structure, thus their chelation may aid in chromatin decondensation.

Methods to terminate the detergent and protease pretreatment include adding proteins to adsorb detergents (such as 0.4% bovine serum albumin, the bovine serum albumin employed at this step should be prepared by dialysis of commercially available BSA fraction V against distilled water to remove soluble salts followed by lyophilization), and adding protease inhibitors (such as soybean trypsin inhibitor) to the reaction. The pretreated nuclei should be subsequently washed using an ice cold solution designed to preserve genomic DNA intactness. NIB buffer can be used for this purpose. NIB is made up of 250 mM sucrose, 25 mM NaCl, 10 mM Pipes, 1.5 mM $MgCl_2$, 0.5 mM spermidine, and 0.15 mM spermine, pH 7.0.

The overall efficacy of mild conditions to obtain a pretreated nucleus can be determined by: a) microscopic examination of nuclei to assess whether nuclei are free of their surrounding cytoskeleton and are free standing or clumped, clumping of nuclei is a strong indication of nuclear damage since many nuclei get trapped in released DNA; and b) the ability of nuclei to respond to activating egg extract, the use of mild conditions increases subsequent activation of individual nuclei and improves the synchrony and homogeneity with which the entire population of nuclei is activated.

(2) Preparation Of Activating Egg Extract

Activating egg extracts can be used to cause non-dividing nuclei to swell, assemble nuclear envelopes and lamina, replicate their genomes, enter mitosis, and form metaphase chromosomes. Activating egg extracts contain material, such as precursors, protein(s), nuclear membrane vesicles, or mRNA required to activate non-dividing nuclei.

Non-activated eggs can be triggered en masse to produce material which brings about activation, by being chemically induced to enter the cell cycle. Eggs can be induced using standard techniques such as electric shock, pricking with a needle, fertilization and the use of a calcium ionophore. (See, Gerhart, et al., *J. of Cell Biology* 98:1247, 1984, and the procedures described below.) The induced eggs enter into the cell cycle. It appears that when an egg is at the point in the cell cycle just prior to the S-phase, the egg cytoplasm is most active in supporting activation. As the egg proceeds into and past the S-phase, it appears to produce material inhibitory to nuclear activation (see Table 1).

One of the benefits of the disclosed procedures is obtaining an activating egg extract having a higher DNA synthesis activation activity than activating egg extract disclosed in the prior art. The DNA synthesis activation activity can be determined by measuring the synthesis of DNA using labelled precursors.

Hardened *Xenopus* eggs are a good source for preparing an activating egg extract. Hardened *Xenopus* eggs are stable for several hours. In contrast, "soft" *Xenopus* eggs must be used rapidly. As soon as soft eggs are dejellied they tend to induce spontaneously and randomly. This is considered disadvantageous because activating egg extracts prepared from a specific time during the cell cycle, just prior to the S-phase, have a higher DNA synthesis activating activity than extracts prepared from other phases of the cell cycle. Thus, it is desirable to synchronously induce a large number of eggs which are all at the same point of the cell cycle, so extracts can be prepared later from a large number of eggs all of which have elevated DNA synthesis activation activity at the same time.

Freshly ovulated *Xenopus* eggs can be hardened by stabilizing the eggs vitelline envelope as described by Wangh, *J. Cell Science* 93:1 (1989). Obtaining freshly ovulated eggs from female *Xenopus* is facilitated by injecting hormones which cause *Xenopus* to ovulate. Injecting 600 units of human chorionic gonadotropin (HCG) into a *Xenopus* female generally brings about ovulation within 12–15 hours. Injection of pregnant mare serum gonadotropin about 24 hours before HCG treatment significantly increases the yield of mature eggs. Furthermore, repeated ovulation of frogs once every 4–8 months improves the yield of eggs by increasing the synchrony of oocyte development in the ovary.

The freshly ovulated eggs within their jelly coat, are flooded with 0.3×NKH (1×NKH is 40 mM NaCl, 2.5 mM KCl, 7.5 mM Hepes, pH 7.4 with NaOH), for 15–20 minutes. During this time the jelly layers swell. The eggs are then dejellied in 3×NKH containing 2% cysteine, pH 7.9, by gentle swirling for about 5 minutes.

The resulting soft eggs can be "hardened" by immediately rinsing them five times in 3×NKH containing 2 mM $MgCl_2$, 1 mM $CaNO_3$, 10 µM $ZnCl_2$ and letting them stand for at least 20 minutes at room temperature. Hardened eggs are sorted to remove damaged and partially induced eggs. Calcium is required for hardening and must be present in the 3×NKH used to wash cysteine-treated eggs. Eggs washed in the absence of $Ca^{2+}$ and subsequently treated with $Ca^{2+}$, and $Ca^{2+}$ treatment of eggs still in the jelly coat, do not result in hardened eggs. Additionally, adding $Ca^{2+}$ before or during dejellying will not result in hardening.

Activating egg extract is preferably obtained from hardened eggs induced en masse. Induction can be carried according to procedures described by Coppock et al., *Developmental Biology* 131:102 (1989). The procedure described by Coppock et al. as modified, in the following manner, was used to obtain "prepared activating egg extract": 5–15 ml of hardened eggs were rinsed using activation buffer (4 mM NaCl, 0.14 mM potassium gluconate, 2 mM Hepes, 2 mM $MgSO_4$, and 0.6 mM $Ca(NO_3)_2$, pH 7.8), and placed in 500 ml of activation buffer; the eggs were then induced by adding calcium ionophore A23187 (10 µM in DMSO; Sigma Chemical Co.) to a final concentration of 100 nM and incubating at room temperature; after 10 minutes calcium ionophore treated eggs were rinsed and induced for an additional 15–20 minutes by incubating in 1.5×NKH containing 2 mM $MgCl_2$, and 0.6 mM $CaCl_2$ (Coppock et al., supra, stops the induction at 10 minutes); the eggs were then placed on ice in a siliconized or teflon beaker and washed 3–5× in several hundred milliliters of ice cold EB buffer (EB=50 mM potassium gluconate, 250 mM sucrose, 10 mM potassium HEPES, 1.5 mM $MgCl_2$, pH adjusted to 7.5 with potassium hydroxide); eggs were then transferred to a volumetric polyallomer centrifuge tube, mixed with Versilube F-50 oil (General Electric) at 0.2 ml oil/ml eggs, and tight packed by centrifugation at 40× g for 1 minute, at 2–4° C.;

the overlaying oil and aqueous layers were removed and the eggs were crushed by centrifugation 15 minutes at 9,000× g, at 2–4° C.; the cytoplasmic layer between the yolk pellet and the overlaying lipid layer was collected from the bottom by puncturing the tube with a syringe needle; cytochalasin B was added to a final concentration of 10–50 μg/ml and the cytoplasmic material recentrifuged for 15 minutes at 9,000× g, at 2–4° C.; the resulting second cytoplasmic supernatant was recovered and either used fresh or frozen for future use.

This procedure for "prepared activating egg extract" involving an increased induction time of 15–20 minutes over that described in Coppock et al. supra, was chosen based upon the following two experiments: 1) plasmid DNA injected into non-activated Xenopus eggs does not begin replicating until 25–30 minutes after eggs are induced, during this lag period factors required for DNA synthesis are possibly released, altered, or synthesized within the egg; and 2) extracts prepared from eggs induced for only 10 minutes synthesize additional proteins in vitro which first act to increase DNA synthesis in pre-treated Xenopus erythrocyte nuclei and then act to inhibit DNA synthesis in these same nuclei.

The second experiment, "induction optimization," is particularly useful in determining the optimal induction time for obtaining activating egg extract having an elevated DNA synthesis activation activity. The experimental results for induction optimization used to obtain an activating egg extract with an elevated DNA synthesis activation activity from Xenopus, is shown in Table 1. The same experimental design could be used to establish the induction time needed to obtain egg extracts having elevated DNA synthesis activation activity from species other than Xenopus.

Induction optimization was carried for Xenopus as describe below (see also Example 2, infra, for further optimization experiments). Xenopus erythrocyte nuclei were isolated and pretreated with lysolecithin and trypsin as described in Example 2 (described below). An activating egg extract was prepared from hardened eggs which were induced for 10 minutes as described above. Both the activating egg extract and the pretreated nuclei were kept on ice (about 4° C.). The activating egg extract was supplemented with 1 mM ATP (not used in the other examples described herein), 10 μg/ml creatine phosphokinase, 10 mM creatine phosphate, 10 μCi $P^{32}$-dCTP and combined with pretreated nuclei (about 200 nuclei/μl). Individual aliquots containing activated nuclei were shifted from 4° C. to 25° C. Cycloheximide to a concentration of 100 μg/ml was added to the individual aliquots at different times. The aliquots were then incubated at 25° C. for a total time, including the time at 25° C. before addition of cycloheximide, of 60 minutes. After 60 minutes, $P^{32}$-dCTP incorporation into newly synthesized DNA was determined.

TABLE 1

| Time CHM Added (Minutes) | Cpm Incorporated into DNA |
|---|---|
| No CHM | 1,296 |
| 0 | 2,894 |
| 5 | 4,208 |
| 15 | 4,937 |
| 30 | 3,775 |
| 45 | 2,314 |

The result of induction optimization for Xenopus activating egg extract is shown in Table 1. The highest observed DNA synthesis activation activity was 15 minutes after the addition of cycloheximide. Thus, about fifteen minutes appears to be the additional time required for peak DNA synthesis activation activity (total induction time of about 25 minutes). A more precise time point for the activation peak may be readily determined by taking additional experimental time points. Elevated DNA synthesis activation activity (more DNA synthesis activation activity than zero time), was seen after an additional 5, 15, and 30 minutes. The elevated DNA synthesis activation activity decreased from 15 to 30 minute time points. After the 45 minute time point the observed DNA synthesis activation activity was below that of the elevated DNA synthesis activation activity. The decrease in DNA synthesis activation activity observed for incubation times longer than an addition 15 minutes is attributed to the synthesis of proteins inhibitory to activation.

As would be appreciated by one skilled in the art, the optimal DNA synthesis activation time will also vary as the temperature changes. As the temperature increases the optimal DNA synthesis activation time decreases, however, the temperature is preferably not raised above 24° C. As the temperature decreases the optimal DNA synthesis activation time increases, however, the temperature is preferably not lowered below 16° C.

Several proteins present in Xenopus egg extracts are involved in DNA replication. One or more of these could be a positive acting protein synthesized during the first 25–30 minutes after activation responsible for the increase in DNA synthesis activation activity. Possible positive acting proteins include: cyclin A, RFA single strand binding protein, cdk2 kinase, and RCC1 protein. There are also several proteins whose synthesis after the first 25 minutes could be responsible for the decrease in DNA synthesis activation activity. Possible proteins which could decrease DNA synthesis activation activity include cdc2 and cyclin B. Given the evolutionary conserved nature of both the positive and negative acting proteins, and their functions, it is likely that eggs from species other than Xenopus also display an optimal time just before the start of S-phase when their cytoplasm is most active in supporting DNA synthesis activation.

As seen in Table 1, incubating for 10 minutes provided less than 60% of the peak DNA synthesis activity observed compared to the optimal DNA synthesis activity of extracts prepared from Xenopus eggs. Using the techniques described herein, the induction time required for obtaining egg extract having an elevated DNA synthesis activation activity (more than 70% of the peak activation) can be obtained for activating egg extract prepared from egg sources other than Xenopus.

Activating egg extracts from "hardened" eggs may be used fresh in which case they support more than one cell cycle in vitro. Alternately, these extracts may be frozen and then thawed, in which case they are able to support one or more cell cycles in vitro.

The activating egg extract is preferably made 7.5–10% (v/v) in glycerol and stored frozen in liquid nitrogen, by standard techniques or by an increased rapid freezing technique. The increased rapid freezing technique freezes the extract faster than merely suspending in liquid nitrogen. Increased rapid freezing can be achieved by spotting extract, made 7.5–10% (v/v) glycerol, as 20 μl droplets onto a block of aluminum immersed in liquid nitrogen.

Before use, frozen activating egg extracts are thawed rapidly at room temperature, put on ice, and if desired, supplemented to enhance activation activity. One possible supplement is cyclic-AMP. The addition of 0.1 mM to 10 mM cAMP to activating egg extracts increases the activation activity of the activating egg extract, as measured by subsequent DNA replication in pretreated *Xenopus* erythrocyte nuclei. cAMP can be broken down by phosphodiesterase. Caffeine is an inhibitor of phosphodiesterase and, thus, enhances the stability of endogenous and added cAMP. Thus, caffeine and phosphodiesterase inhibitors are possible supplements to enhance activation activity of activating egg extract. Indeed, the addition of caffeine to activating egg extract was found to increase subsequent DNA replication in activated *Xenopus* nuclei.

Appropriate egg extracts can be obtained from sources other than *Xenopus*. Useful guidelines for choosing an appropriate egg source to make either activating egg extract or CSF extract are provided below. These guidelines are not intended to be a list of required characteristics, but rather a list of considerations useful for choosing an egg source.

Useful guidelines for choosing an appropriate egg source for making egg extracts include the following:

1. Egg/embryo with substantial stores of activating cell cycle material are preferred. Such egg/-embryos can be identified as those showing a series of rapid cell cycles, i.e., cell divisions approximately once every hour as compared to once every day.

2. Moderate egg size is preferred. Moderate egg size represents a compromise between the cytoplasmic volume per egg and yolk mass per egg. Preferably a large yield of cytoplasm per volumetric measure of eggs is obtained.

3. A species in which female animals shed a large number of eggs is preferred as a means of increasing the amount of egg extract available from an animal, while keeping the cost of caring for the animal at a minimum. However in some instance, such as the activation of mammalian somatic cell nuclei prior to transplantation into their corresponding eggs, it may be desirable to prepare extracts from mammalian eggs despite their small size and relatively small number per female.

4. Females of the chosen species are preferably identifiable by external characteristics.

5. Females preferably breed in a reasonable period of time (at least once per year), and at a reasonable cost.

6. Eggs are preferably shed as single cells (e.g., not in jelly mass), or easily freed of jelly layers and other major external envelopes.

7. Eggs can preferably be stabilized from activating once freed of extracellular coats. (see e.g., Wangh, *J. Cell Science* 93:1 (1989)).

8. Females preferably produce high quality eggs which are uniform and regular. These features minimize waste and help in developing automated methods to sort good and bad eggs. Some eggs, such as those of echinoderms and mollusks, are transparent and contain a prominent germinal vesicle nucleus which can be used to judge egg quality. Other eggs, such as those of *Xenopus*, are not transparent, but have two distinct colors which can also be used to judge egg quality.

9. Eggs are preferably chemically inducible in a synchronous manner such that a number of eggs may be induced at the same time and be approximately at the same point in the cycle at a specified later time (preferably at meiotic metaphase state or mitotic metaphase state). In this way, extracts may be obtained from a number of eggs at the same point in the cell cycle by inducing all the eggs at one time and using all the eggs to prepare an extract at a later time.

10. Females can preferably be chemically induced to ovulate thereby making it possible to increase the production of eggs from a given female.

11. Female are preferably not harmed by the egg collection method. Alternately, if egg collection does harm the female those females for which a commercial use of the carcass exists are preferred.

12. Preferably the eggs allow preparation of extracts that induce nuclear swelling, either without or with concomitant DNA replication. Nuclear swelling without replication can be achieved by removal of membrane vesicles required for nuclear envelope assembly, or by inhibition of DNA synthesis (e.g., using reagents such as aphidicolin, mimosine, or DMAP), or by CSF extract supplemented with a kinase inhibitor (e.g., such as DMAP or staurosporine). Nuclear swelling with replication can be achieved using activating egg extracts such as those obtained from *Xenopus* eggs.

13. It is important that eggs used to prepare CSF extracts can be arrested in either the meiotic metaphase state, or in the mitotic metaphase state. Recovery of chromosomes, rather than interphase nuclei, requires cell cycle arrest in metaphase. For some species, extracts in metaphase arrest can be prepared directly from non-activated eggs, such as unfertilized *Xenopus* eggs, or can be made to cycle into and arrest in meiotic metaphase. Useful reagents for bringing about and causing arrest in meiotic metaphase include cyclin Δ90 (a non-degradable form of sea urchin cyclin), other cyclin related peptides, small amounts of CSF extract (prepared from non-activated *Xenopus* eggs), components found in non-activated *Xenopus* eggs (such as c-MOS kinase) or Calyculin A used on echinoderm eggs (Tosuji et. al. *Proc. Natl. Acad. Sci.* 89:10613 (1992)).

(3) CSF Extract Treatment Of Nuclei

Non-activated CSF extract can be used to aid subsequent nuclear activation of non-dividing mammalian cell nuclei, including human cell nuclei, without directly causing nuclear swelling or DNA replication; or to directly cause nuclear swelling as discussed in section II infra. Nuclei in CSF extract appear to condense into chromosome like structures and may become surrounded by a spindle apparatus. Nuclear activation prior to contact with an activating egg extract is disadvantageous. Problems with premature activation include a decrease in the enhancement of activation and different nuclei being activated at different times.

The ability of CSF extract to enhance activation may be increased by various supplement. In addition, the incubation conditions of nuclei in CSF extract can be adjusted to improve the ability of such extracts to enhance activation of the nuclei upon subsequent contact with activating egg extract.

The CSF extract is preferably prepared from non-induced eggs arrested at meiotic metaphase. CSF extract prepared from non-induced eggs arrested at meiotic metaphase contain high levels of mitosis promoting factor (MPF) activity and cytostatic factor (CSF) activity. CSF and MPF are factors present in CSF extract which are believed to aid in subsequent activation of quiescent nuclei by altering cytoskeletal proteins, nuclear matrix proteins, and nuclear histones, particularly by phosphorylation of these proteins.

MPF is an activity controlling nuclear entry into mitosis and initiation of spindle assembly. MPF is composed of two catalytic subunits, $p34^{cdc2}$ and cyclin B. At the onset of anaphase, cyclin B is destroyed resulting in the inactivation of MPF. During anaphase the chromosomes move towards the two opposite poles of the spindle apparatus and subsequently decondense.

CSF is an activity responsible for metaphase arrest in unfertilized vertebrate eggs. CSF activity is due to at least two kinases: mitogen-activated kinase (MAP) and cdk2/cyclin (cdk2 is a kinase related to cdc2, but the regulatory subunit of cdk2 is cyclin E (or A) rather than cyclin B). The activities of MAP appears to be controlled by additional kinases such as c-Mos kinase.

One reason for obtaining CSF extract from eggs arrested at meiotic metaphase, is that both MPF and CSF are inactivated upon initiation of the cell cycle.

CSF extracts from non-induced *Xenopus* eggs can be prepared by a method based on the work of Lohka and Masui, *Developmental Biology* 103:434 (1984), as well as that of Murray et al., *Nature* 339:280 (1989). A procedure for obtaining CSF extract is as follows. Eggs are obtained from one or more ovulating frogs as described above. Each batch of freshly ovulated eggs, about 500 to 1000 eggs, is hardened as described above. Damaged and activated eggs are removed. The remaining eggs are combined into a large siliconized glass or teflon beaker and washed 4–5 times at room temperature (about 21° C.) in approximately 500 ml EB-buffer containing 5 mM potassium EGTA, pH 7.5, (EB=50 mM potassium gluconate, 250 mM sucrose, 10 mM potassium HEPES, 1.5 mM $MgCl_2$, pH adjusted to 7.5 with potassium hydroxide). The eggs are then transferred to a volumetric polyallomer centrifuge tube, mixed with Versilube F-50 oil (General Electric) at 0.2 ml oil/ml eggs, and are tight packed by centrifugation at 40× g for 1 minute, at room temperature. The overlaying oil and aqueous layers are removed and the eggs are crushed by centrifugation for 15 minutes at 9,000× g, at 2–4° C. The cytoplasmic layer between the yolk pellet and the overlaying lipid layer is collected from the bottom by puncturing the centrifuge tube with a syringe needle. Cytochalasin B is added to a final concentration of 10–50 $\mu$g/ml and potassium EGTA is added to a final concentration of 1 mM. The cytoplasmic material is mixed by gently pipetting or rocking back and forth, the cytoplasmic material is then centrifuged for 15 minutes at 9,000× g, at 2–4° C. An alternative centrifugation procedure involves preparation of a high speed supernatant by centrifugation at >100,000× g for 2 hrs at 2–4° C. In either case, the resulting second cytoplasmic supernatant (hereinafter "prepared CSF extract") is recovered and is either used fresh or is made 7.5–10% in glycerol and frozen for future use in the same manner as activating egg extract. Preferably, CSF extract is incubated at 25° C. for 2 hours prior to freezing. The level of histone H1 kinase activity increases several fold during the period of incubation.

Frozen extracts can be used by thawing rapidly at room temperature and then placing on ice. Thawed extracts are preferably supplemented with an ATP regenerating system consisting of 10 mM creatine phosphate, and 10 $\mu$g/ml creatine phosphokinase.

The histone H1 kinase activity, the structural state of plasmid DNA added to the CSF extract, and the inability of CSF extract to cause nuclear activation, demonstrated that "prepared CSF extract" was arrested in meiotic metaphase. The histone H1 kinase activity of the CSF extract either before or after freezing was high. Upon activation of the extract with 1.2 to 4 mM $Ca^{2+}$, the histone activity decreased. Preferably, 1.2 mM $Ca^{2+}$ is used when CSF extract is supplemented with 1 mM EGTA to achieve recycling. No recycling occurs when 3 to 4 mM of $Ca^{2+}$ is used in CSF extract supplemented in the presence of 1 mM EGTA. Negatively supercoiled circular plasmid DNA added to the extract relaxed. Lysolecithin-trypsin pretreated *Xenopus* erythrocyte nuclei added to CSF extract failed to swell or synthesize DNA.

After further pretreatment in CSF extract, the nuclei may be activated by adding 9 volumes of "prepared activating egg extract." DNA replication, measured by incorporation of labelled nucleotides into DNA strands, may be used to determine the extent to which prior treatment in CSF extract enhances nuclear activation in activating extract. Labelled nucleotides useful in measuring nuclear DNA replication include microcurie amounts of $P^{32}$-dCTP for radioactive measurement of newly synthesized DNA, 16–50 $\mu$M biotinylated-dUTP or BrdUTP for fluorescent measurement of newly synthesized DNA, and 250 $\mu$M BrdUTP for density labelling of newly synthesized DNA.

Several supplements to CSF extract, in the proper concentration, increased the ability of CSF extract to enhance activation activity without resulting in premature DNA synthesis activity. Useful supplements include $\beta$-glycerol-$PO_4$, $Ca^{2+}$, and protein kinase inhibitors. The addition of $\beta$-glycerol-$PO_4$ increased the rate at which negatively supercoiled DNA relaxed in CSF extract and was subsequently assembled into chromatin. A concentration of about 80 mM $\beta$-glycerol-$PO_4$ was found to aid in chromatin assembly without causing DNA synthesis. Beta-glycerol-$PO_4$ is an inhibitor of phosphatase activity and may act by increasing the level of the phosphorylated functionally-active form of topoisomerase II in the CSF extract.

Similarly, the addition of 100 $\mu$M $Ca^{2+}$ increased both the rate negatively supercoiled DNA relaxed in CSF extract and rate of subsequent assembly into chromatin. Calcium is a cofactor for calcium calmodulin activated protein kinases and may also act by increasing the level of phosphorylated active topoisomerase II activity in the CSF extract. The addition of 100 $\mu$M $CaCl_2$ to thawed CSF extract failed to trigger its entry into the cell cycle as judged by continued high levels of histone H1 kinase activity. The addition of 100 $\mu$M $Ca^{2+}$ also increased both the amount and the rate of DNA synthesis in erythrocyte nuclei after addition of activating egg extract. CSF extract responded to the addition of 1.2–4 mM $Ca^{2+}$ by increasing the rate and extent of chromatin assembly over that seen upon addition of 100 $\mu$M $Ca^{2+}$. However, the higher concentration of calcium also activated the CSF extract.

The association of factors, whose presence increase DNA synthesis activity of CSF extract was also examined. Apparently, one or more factors in CSF extract which aid in subsequent DNA replication are loosely held by the nuclei in CSF extract and are lost during washing. *Xenopus* cell nuclei were pretreated with trypsin and lysolecithin, added to CSF extracts to a concentration of 1000–2000 nuclei per $\mu$l, and either washed by diluting into excess NIB buffer and centrifuging, or not washed. Subsequent addition of activating egg extract, to a concentration of 100–200 nuclei per $\mu$l, resulted in less DNA replication for washed nuclei. For this reason, CSF extracted treated human nuclei are preferably not washed prior to contact with activating egg extract.

Nuclear activation upon contact with activating egg extract can be increased by manipulating the conditions in which nuclei are incubated in CSF extract during further pretreatment. Useful manipulations can be obtained by regulating the incubation period and temperature. The use of a warm-then-cold regime stimulates subsequent nuclei activation. Both warm and cold steps appear to exert positive effects on subsequent nuclei activation. Preferably, the warm-then-cold regime comprises incubation at about 25° C. for 30–90 minutes followed by incubation at 4° C. for 30–90 minutes.

Trypsin and lysolecithin treated *Xenopus* red blood cell nuclei incubated in frozen/thawed CSF extract using a warm-then-cold regime and contacted with fresh activating egg extract resulted in extensive and synchronous nuclear envelope formation, swelling, and replication upon contact with freshly prepared activating egg extract. While this system is attractive to aid in activation of human nuclei, because of the convenience of using frozen CSF extract, use of this system on *Xenopus* erythrocyte nuclei revealed several limitations. One limitation is the need to freshly prepare activating egg extract, which is experimentally inconvenient.

Using $CaCl_2$ in conjunction with frozen CSF overcomes this limitation. The use of $CaCl_2$ permits synchronous nuclear envelope formation, swelling, replication, entry into mitosis (including formation of chromosome-like structures without DNA fragmentation), and renewed DNA synthesis in a second S-phase when both frozen CSF and frozen activating egg extracts are used. Thus, the use of both a warm-then-cold regime and $CaCl_2$ is particularly advantageous when frozen activating egg extracts and frozen CSF extracts are used to cause nucleus activation. Preferably the CSF extract contains 0.1 to 0.4 mM $CaCl_2$ to enhance nuclear activation upon subsequent contact with activating egg extract. At this range of $Ca^{2+}$, nuclei treated in CSF extract should not activate until contact with activating extract.

(4) Activation Of Nuclei With Activating Egg Extract

Activating egg extracts can be used to activate non-dividing mammalian cell nuclei, such as non-dividing human cell nuclei, to bring about swelling, chromatin decondensation, DNA replication and formation of metaphase chromosomes. However, nuclear activation can be stopped at various points and information about nucleic acid sequence and structure can be obtained by examining the resulting DNA. Under duplication conditions, the nucleus swells, DNA replicates, and the resultant chromosomes divide. Under non-duplication conditions, the nucleus swells, DNA is replicated, but the resultant chromosomes do not divide. Under non-synthesis conditions the nucleus swells, but DNA is not replicated, and nuclei do not divide.

The use of nocodazole, or other drugs like colchine, colcemid, and $D_2O$ which inhibit microtubule assembly is preferred for preventing separation of mitotic chromosomes. These drugs prevent the formation of mitotic spindles during the cell cycle. As a result, condensed chromosomes accumulate rather then separate to the cells poles and are readily visualized for karyotypic analysis.

However, the addition of 5 µg/ml nocodazole to activating egg extract decreases the rate of DNA replication. Thus, to maintain a high rate of DNA replication it is necessary to either: 1) use nocodazole at a dose less than 5 µg/ml, such as adding nocodazole to CSF extract at 5 µg/ml and diluting the mixture with 9 volumes of activating egg extract; 2) use another drug such as colchine, colcemid or $D_2O$ (deuterium oxide) which may be able to block mitotic spindle formation without inhibiting DNA replication; or 3) add the spindle inhibitor later, i.e., after DNA synthesis is complete but before nuclei proceed into mitosis.

To avoid artifacts such as chromosome fragmentation during nuclear activation it is desirable that complete, rather than partial, replication of nuclear genomes be achieved. The following techniques are useful to assess the extent of genome replication achieved during nuclear activation:

1) Coordinate observations of the kinetics of DNA synthesis, the size of the DNA molecules made, the timing of mitosis following DNA synthesis, and the morphological appearance of nuclei. Complete replication is characterized by a early onset and rapid rate of DNA synthesis in all nuclei, an abrupt cessation of DNA synthesis in all nuclei, followed by rapid entry into mitosis, and renewed replication when nuclei exit mitosis. In addition, newly synthesized DNA molecules are very long (greater than 50,000 base pairs), but are transiently cleaved by type II topoisomerase during the period of chromosome condensation and decondensation.

2) The isotope dilution technique can be used to measure the pool size of DNA precursors in the activating egg extract to establish the extent of genome replication, on the basis of the radioactive specific activity of the DNA. The isotope dilution technique can be carried out according to Blow and Laskey, *Cell* 47:577 (1986).

3) BrdUTP density labelling of newly replicating DNA followed by isopycnic centrifugation in CsCl and Southern hybridization can be used to determine if one or more rounds of replication is occurring. During the initial round of semi-conservative replication, incorporation of BrUTP leads to formation of a DNA duplex having one heavy (BrUTP containing) strand and one light strand. The subsequent production of a DNA duplex containing two heavy strands indicates more than one round of replication.

4) DNA replication can be visually measured using biotinylated-deoxynucleotide triphosphates (such as biotin-11-dUTP) or bromodeoxy-UTP. These labeled nucleotides can be added to activating egg extracts and are incorporated into DNA during replication. Nuclei containing the labelled DNA can be recovered and examined in a fluorescent microscope. The labelled DNA is conveniently visualized by staining with Texas Red streptavidin (for biotin samples) or FITC (fluorescein) anti-BrdUTP antibodies. Total DNA can be visualized using a fluorescent intercalating dye (such as propidium iodide or Hoechst stain) or a fluorescently tagged reagent. In some cases it may be desirable to treat nuclei in the microchamber microscope slide with high salt solutions to stretch the DNA across the glass surface before DNA staining. A fluorescent microscope can be employed to establish whether all regions of the nuclear DNA (stained for instance with Hoechst) contain newly synthesized DNA (stained for instance with biotin-Texas Red streptavidin)

II. Use of a CSF Extract to Cause Nuclear Swelling

Nuclear swelling can be brought about in non-dividing nuclei by using a modified CSF extract, made by high or low speed centrifugation, or by using a CSF extract or modified CSF extract made by high speed centrifugation (a "partially purified CSF extract"). Use of a CSF extract to induce nuclear swelling is preferably carried out on isolated nuclei pretreated to separate the nuclei from its surrounding cytoskeleton, preferably with detergent and a protease as described herein. Preferably, the modified CSF extract is a partially purified CSF extract and is modified by either (a) diluting with an aqueous solution and/or (b) supplementing with a protein kinase inhibitor. Fresh CSF extract or frozen thawed extract can be modified.

Dilution of CSF extract to enhance its ability to cause nuclear swelling may be carried out using various aqueous solutions such as water and physiological pH buffers. The aqueous solution is preferably buffered to about pH 6.5 to about pH 7.5. An example of an appropriate buffer is EB buffer (EB=50 mM potassium gluconate, 250 mM sucrose, 10 mM potassium HEPES, 1.5 mM $MgCl_2$, pH adjusted to 7.5 with potassium hydroxide). Preferably, the aqueous solution is added in an amount to achieve 25% to 75% dilution.

The ability of CSF extract to cause nuclear swelling can also be enhanced by using a protein kinase inhibitor such as DMAP or staurosporine. DMAP and staurosporine are broad range kinase inhibitors able to inhibit the actions of both CSF and MPF. Other protein kinase inhibitor able to inhibit CSF and/or MPF can be obtained by one skilled in the art. The chosen kinase inhibitor can preferably inhibit both CSF and MPF.

Preferably, 2.5–5 mM of DMAP is used. The use of protein kinase inhibitors should block kinase activities in the extract, including histone H1 kinase and result in the treated nuclei forming envelopes but failing to initiate DNA replication. The proper protein kinase inhibitor concentration can be empirically determined by one skilled in the art by measuring the extent of swelling and DNA replication in the presence of different amount of protein kinase inhibitors.

Preferably, an aqueous solution and a protein kinase inhibitor are both used to modify CSF extract. Nuclei treated with diluted CSF extract supplemented with DMAP (CSF-DMAP) swell to a greater volume than nuclei treated with undiluted CSF-DMAP. Preferably, CSF containing a protein kinase inhibitor (CSF-PKH) is diluted 25% to 75% using an appropriate buffer and nuclei are incubated for more than 60 minutes at 25° C., and more preferably around 90 minutes at 25° C. prior to measuring nuclei swelling.

Diluted CSF-PKH extract can be further modified by altering the $Ca^{2+}$ and $Mg^{2+}$ ion concentration to further increase swelling, and affect chromatin condensation and decondensation. $Ca^{2+}$ and $Mg^{2+}$ ion concentration can be altered by addition of these ions or by removal of these ions by using chelating agents, such as ethylene diaminetetraacetic acid (EDTA) (e.g., 5 mM), or ethylene glycol-bis(β-aminoethyl ether)N,N,N',N'-Tetraacetic Acid (EGTA) (e.g., 5 mM). Altering the free $Ca^{2+}$ and $Mg^{2+}$ ion concentration in the diluted CSF-PKH has the effect of changing the extent of nuclear swelling and the appearance of the chromatin within the nucleus. Very low or absent $Ca^{2+}$ and $Mg^{2+}$ ion levels enhance nuclear swelling and chromatin decompaction. Increasing $Ca^{2+}$ to 1.2 mM prevents significant nuclear swelling and chromatin decompaction. The optimal amount of $Ca^{2+}$ and $Mg^{2+}$, and chelator can be empirically determined by varying the amount of chelator and cation concentration and measuring nuclei swelling.

Chelating agents or other agents which cause chromatin decondensation, such as polyanions like heparin and TPP or thiol reducing agents like DTT, need not be added directly to the diluted CSF-PKH extract. These additional agents may be used to further swell or decondense the nuclei after treatment in diluted CSF-PKH extract.

III. Use of a CSF Extract Supplemented with a Cyclin

A CSF extract supplemented with a cyclin can be used to induce chromosome formation without DNA replication. The CSF extract should be supplemented with a cyclin such as cyclin-Δ90 in an amount sufficient to achieve both nuclear envelope breakdown and nuclear chromosome formation. The cyclin is expected to act by raising the level of MPF activity in CSF extracts, and thereby, induce conversion of isolated nuclei into mitotic chromosomes.

CSF extract supplemented with cyclin was used to activate nuclei in suspension resulting in nuclei conversion into chromosomes. However, the activation also resulted in intermingling of the formed chromosome, and the chromosomes were stretched and sheared. The use of CSF extract supplemented with cyclin-Δ90 may be improved by sticking trypsin treated nuclei to a glass surface prior to incubating with modified CSF.

IV. Activation of Mammalian Sperm

The present invention also features a method for activating mammalian sperm, which is particularly suitable for the activation of human sperm. The method involves the pretreatment of human sperm with a protease, then activating the sperm with an activating egg extract. The present disclosure is believed to be the first describing the use of trypsin and an activating egg extract to activate a human sperm. The pretreated sperm can be activated using activating egg extract, or the various procedures described herein, such as using a modified CSF extract (e.g., supplemented with an aqueous solution and/or a protein kinase inhibitor, or supplemented with a cyclin) to achieve nuclear swelling or chromosome formation, and using both a CSF extract and activating extract to cause nuclear activation.

The preferred method for activating a sperm involves (1) pretreatment involving a protease, a detergent, a thiol reducing agent, and preferably a thiol blocking to prevent reassociation of sulfhydryl groups; (2) further pretreatment using CSF extract; and (3) activation using an activation extract. Sperm can be obtained using techniques known in the art. Pretreatment can be carried out using a protease and a detergent either sequentially, or at the same time, followed by a thiol reducing agent, followed by a thiol blocking agent.

An example of a preferred protocol is as follows:

1. Lyse sperm in 100 μg/ml lysolecithin for 5 min at 25° C.
2. Treat with 100 μg/ml trypsin for 5–15 minutes (10 minutes is optimum) at 25° C.
3. Stop the lysolecithin and trypsin treatment by using 30 μg/ml soybean trypsin inhibitor and 0.4% bovine serum albumin.
4. Incubate sperm nuclei in 5 mM dithiothreitol for 60 minutes at 4° C.
5. Stop reaction 4 by incubating nuclei in 1 mM N-ethylmaleimide for 10 minutes at 25° C.
6. Incubate nuclei in CSF extract for 90 min at 25° C., followed by 60 minutes at 4° C.
7. Incubate nuclei in activating egg extract.

The above procedure results in nuclear swelling without nuclear envelope formation during the CSF pretreatment step (step 6), and additional swelling, nuclear envelope formation, and DNA replication during the activating egg extract step (step 7). Steps 1–3, or their equivalent, are all required to achieve complete swelling, nuclear envelope formation, and DNA replication.

Activation of sperm cells have various uses including being used to determine whether the sperm contains a particular gene or nucleic acid sequence which can be passed on during fertilization. Such studies are useful, for example, to study the effect of aging on sperm; detect chromosomal defects; and determine whether foreign genes (such as those present in the human immuno deficiency virus (HIV)) are present is sperm.

An example of the usefulness of this aspect of the invention is in the field of animal breeding, particularly the breeding of transgenically modified animals. Transgenically modified animals are usually created by injecting DNA sequences into early embryos. If the injected DNA integrates into the host cell genome, it may end up in the germ line of the adult animal after the animal matures. Transgenic male animals are particularly desirable since they can be bred to many females. However, prior to breeding the percentage of modified germ cells, as well as the copy number and distribution of the inserted genes in each cell is not known.

The methods and reagents provided herein for activating sperm cell nuclei and examining their genetic composition, for example via in situ hybridization, make it possible to determine the percentage of sperm carrying one or more copies of the inserted gene. This information can used to access the likelihood that a particular gene will be passed on to a future generation, prior to breeding the animal. Such information is desirable because of the time and expense required to breed an animal.

V. Nuclear Activation Assay

The procedures disclosed by the present invention, to activate nuclei, can also be used as a general assay procedure to measure nuclear activation and the presence of a nucleic acid sequence in activated nuclei. The assay would be particularly useful to identify and purify factors present in CSF extract and to study male fertility.

A basic assay to measure DNA replication of activated cell could have the following steps: isolating a nucleus, pretreating the nucleus, further pretreating the nucleus, contacting the further pretreated nucleus with activating egg extract containing labeled nucleotides, and detecting incorporation of label into replicated DNA. Preferably, a radioactive nucleotide would be used to determine activation by measuring the extent of label incorporated into newly synthesized DNA.

The assay could be tailored to aid in the purification of factors present in CSF which help prepare nuclei for subsequent activation. Specifically, the assay would be performed without the addition of CSF extracts. Rather, various fractions of CSF extract would be obtained by standard purification techniques, and used instead of CSF extract. Those fractions which increase activation activity can then be further purified.

Another use of a nuclear activation assay is to study male fertility by measuring the extent of activation of human sperm under different conditions. Such studies can be used, for example, to examine techniques to preserve sperm so the sperm can be later used in in vitro fertilization, to test sperm of infertile men to identify causes of male infertility (see, Brown et al., *Yale Journal Of Biology And Medicine* 65:29 (1992) (not admitted to be prior art), and test possible male contraceptives.

In virtually all species of animals, sperm cells undergo two reactions, capacitation and the acrosome response, before reaching and fusing with the egg surface. After the sperm nucleus enters an egg it undergoes several changes. The nucleus swells, acquires a nuclear envelope and lamina, replicates its DNA, and eventually fuses with the female pronucleus. During this process, sperm basic proteins (histones and protamines), are exchanged for embryonic histones.

It appears that in order for a sperm nucleus to respond to an egg cytoplasm it must first undergo some form of proteolytic digestion. A likely site of necessary proteolytic digestion are non-histone cytoskeletal proteins. Possible contraceptives could target necessary proteolytic enzymes. The affect of the contraceptive could be determined by assaying the degree to which activation is inhibited. Possible contraceptives could also target other enzymes which may be needed for activation.

Alternatively, the assay could be used to determine conditions which result in higher levels of activation thereby finding conditions which enhance fertilization.

Specific uses of the nuclear activation assay include the following:

1) Assaying sperm cell treated under different conditions of preparation, cryopreservation, capacitation and handling;

2) Assaying the affect of sperm cell enzymes (e.g., proteases, nucleases, phosphatases, and kinases), including the inhibition of sperm cell enzymes, on activation;

3) An assay to purify enzymes affecting activation;

4) Assaying the sperm from infertile individuals to determine if infertility is due to problems with sperm nuclear activation;

5) Assaying the ability of specific drugs or reagents to enhance or inhibit activation;

6) Assaying the affect of inhibitors or activators of sperm cell enzymes on activation;

7) Assaying for the presence of a gene used to create a transgenic animal; and

8) Assaying for the presence of viral genome, such as HIV present in sperm.

The specific nuclear activation assay used to study fertility would be tailored to study a particular aspect of activation. For example, to assay the effect of reagents on activation the sperm should be handled and prepared under mild conditions. As discussed above mild conditions are useful in minimizing inadvertent activation of proteases or nucleases. To obtain sperm for the activation assay, fresh sperm samples should be first washed in isotonic saline solution under mild conditions. The sperm can then be stored by freezing in liquid nitrogen under controlled conditions in the presence of a cryoprotectant. Martin et al., in *PREIMPLANTATION GENETICS*, Plenum Press, New York (Verinsky and Kuliev, eds, 1991).

Fresh or frozen/thawed sperm can be treated under conditions which result in capacitation as described by Martin et al. *Supra*. The sperm membrane is then permeabilized under mild conditions as described above (e.g., lysolecithin is used to permeabilize the membrane). The nuclei are then recovered from lysed sperm by mild centrifugation in isosmotic buffer. Nuclei are preferably pretreated as described above in Section II (e.g., using a membrane permeabilizer, a protease, and a thiol reducing agent).

The nuclei can then be further pretreated (e.g., using CSF extract containing 100 $\mu$M $Ca^{2+}$). The further pretreated nuclei are contacted with activating egg extract and activation activity is measured using standard techniques such as using a labeled reagent (e.g., $P^{32}$-CTP) to detect DNA replication, and microscopic visualization of nuclear swelling. Additionally, in situ hybridization can be carried out to determine the presence, number and location of particular DNA sequences. The effect of various reagents on nuclear activation can be determined by adding reagents to the sperm before or after the various individual steps of isolation, pretreatment, further pretreatment or contact with activating egg extract.

VI. Retroviral Integration Assay

The assays described herein can be used to examine integration of proviral nucleic acid, such as from HIV, into host DNA. The assays can be carried out using a whole nucleus or a pseudonucleus. Such assays can be used to identify target sites to inhibit proviral integration, and to derive anti-viral agents directed at such target sites.

A provirus is the double-stranded DNA form of a retrovirus. It is synthesized in the cytoplasm of a cell infected with a retrovirus by reverse transcription of the viral RNA. Integration of the provirus DNA into the host cell genome is a critical step in the life cycle of all retroviruses, including HIV-1, and leads to viral expression and new virus production. Thus, by blocking viral integration, viral propagation (e.g., viral multiplication and/or viral infection) can be inhibited.

An integration assay can be performed as follows:

1. A cell nucleus is pretreated to separate the nucleus from its surrounding cytoskeleton to form a pretreated nucleus. The choice of cell nucleus can be varied depending on the virus studied. Preferably, the cell nucleus will be obtained from a cell which is a natural host for the virus. Examples of cells susceptible to retroviral infection include mammal and plant cells. Preferably, a human cell nucleus is used.

2. The pretreated nucleus is activated and incubated with a viral integration complex. A viral integration complex contains the proviral double stranded DNA form of the viral RNA and material needed for viral integration. Thus, the integration complex contains an integrase and may contain other viral enzymes and proteins. An integration complex can be obtained by one skilled in the art using standard techniques. For example, a high speed supernatant of cells infected with a virus can be used as an integration complex. (Brown, et al., Cell 49:347, 1987). Alternatively, an integration complex can be obtained from purified viral integrase and specific oligonucleotides having the viral sequences needed for integration (Engelman et al., Cell 67:1211, 1991). The integration complex can be added to nuclei, chromatin or pseudonuclei, at different points in the cell cycle. For example, incubation can take place before (e.g., prior to activation), during the time that nuclei are swelling and forming nuclear envelopes in CSF extract and activating extract, or during chromatin assembly, nuclear envelope formation or replication of pseudonuclei.

3. Measuring integration of the viral nucleic acid into the host nucleic acid. The measurement can be carried out using standard techniques such as through the use of hybridization probes targeted to viral nucleic acid sequences. The use of hybridization probes can be facilitated by amplification techniques such as PCR amplification. Preferably, unintegrated viral nucleic acid is separated from host nuclei acid prior to using the hybridization assay probe. A separation step is useful for decreasing hybridization of probes to viral nucleic acid not incorporated into the host genome. Separation can be carried out, for example, by centrifugation of nuclei through glycerol or electrophoresis of isolated nucleic acids.

Alternatively an integration assay can be carried out using a pseudonucleus. A pseudonucleus can be constructed from a plasmid DNA template which is then used as a target for retroviral integration rather than intact activated nucleus. This approach has the advantage that the oligonucleotide size of the plasmid genome is much smaller than that of a whole eukaryotic nucleus and the sequence of the plasmid genome is either known or can be readily established.

A pseudonucleus can be constructed by adding plasmid DNA to a fresh or frozen/thawed CSF extract (e.g., at 0.1–20 ng/$\mu$l). This material can be used immediately or frozen for latter use. The plasmid DNA can form chromatin in the CSF extract. (For example, see Sanchez et al., Journal of Cell Science 103:907, 1992 and Wangh, Journal of Cell Science 93:1, 1989, describing such chromatin formation using plasmid FV1 dervived from type 1 BPV in intact Xenopus eggs).

The assay is carried out by activating the chromatin and measuring integration of viral nucleic acid. For example, the chromatin is diluted into an additional sample of CSF extract which is activated (e.g., by the addition of 1.2 mM $Ca^{2+}$). Activation triggers nuclear envelope formation around the chromatin and causes the chromatin to replicate.

Thus, an activation assay can be performed using a pseudonucleus in place of a pretreated nucleus as follows: 1) forming a pseudonucleus; 2) activating the pseudonucleus, and incubating with an integration complex containing viral nucleic acid before activation or at different times after activation; and 3) measuring integration of the viral nucleic acid into the nucleic acid of the pseudonucleus.

Using an integration assay, it can be determined when viral integration occurs during the cell cycle, and if an agent is effective in inhibiting viral integration. For example, the importance of different stages of the cell cycle in viral integration can be evaluated using CSF or activating extracts supplemented with DMAP, aphidicolin, and inhibitors of type II topoisomerase. DMAP and aphidicolin block DNA replication but allow nuclear swelling and chromatin decondensation to proceed. Inhibitors of type II topoisomerase block chromatin decondensation, which requires type II topoisomerase activity. Examples of the use of such drugs include the following:

1) If drugs such as DMAP and aphidicolin inhibit chromatin decondensation but fail to inhibit viral integration, then chromatin decondensation after mitosis is probably all that is necessary for integration. In this instance, drugs could be designed to prevent integration during or prior to chromatin decondensation.

2) If integration (i.e., insertion of the proviral DNA into the target genome) and circularization (i.e., insertion of the proviral DNA into itself) are both blocked by DMAP and aphidicolin, then on-going DNA synthesis is probably required for viral integration. Accordingly viral integration during DNA synthesis could be targeted. If DNA synthesis is required for proviral integration, it can then be determined whether integration occurs before or after the host genome target is replicated. For example, bromodeoxyuridine triphosphate (BrdUTP) can be added to reactions to increase the density of newly synthesized DNA strands. Samples can then be collected at the end of the S phase when genome replication is complete. After electrophoretically removing all unintegrated viral molecules, the genomic DNA can then be cleaved with a restriction enzyme that recognizes two or more sites within the viral genome. The preparation can then be fractionated, for example, by CsCl density gradient centrifugation and probed for released segments of the virus. If the provirus is inserted into the host genome before replication, the viral DNA will be recovered in the heavy/light density peak, along with virtually all the genomic DNA. On the other hand, if the provirus is inserted after its target sequence has replicated, the viral DNA will be in the light/light peak. After determining the timing of integration, drugs can be designed to inhibit integration and tested.

3) If integration takes place in the presence of DMAP or aphidicolin, but not both, this would indicate that DNA synthesis, per se, is not required for integration, but cell cycle-dependent properties of the cytoplasm influences integration.

Thus, using this application as a guide, one skilled in the art can identify when, during the life cycle of a cell, viral integration occurs, target drugs to inhibit such viral integration, and assay whether an agent inhibits viral integration. Agents which inhibit retroviral integration may be used as therapeutic agents to treat a person infected with a retrovirus (such as HIV) or prevent an uninfected person from being infected with a retrovirus. A retroviral "therapeutic agent" refers to an agent which reduces, to some extent, the in vivo propagation of a retrovirus and preferably reduces, to some extent, one or more of the symptoms associated with a retroviral infection.

VII. Microchamber Microscope Slide

Figure 4:
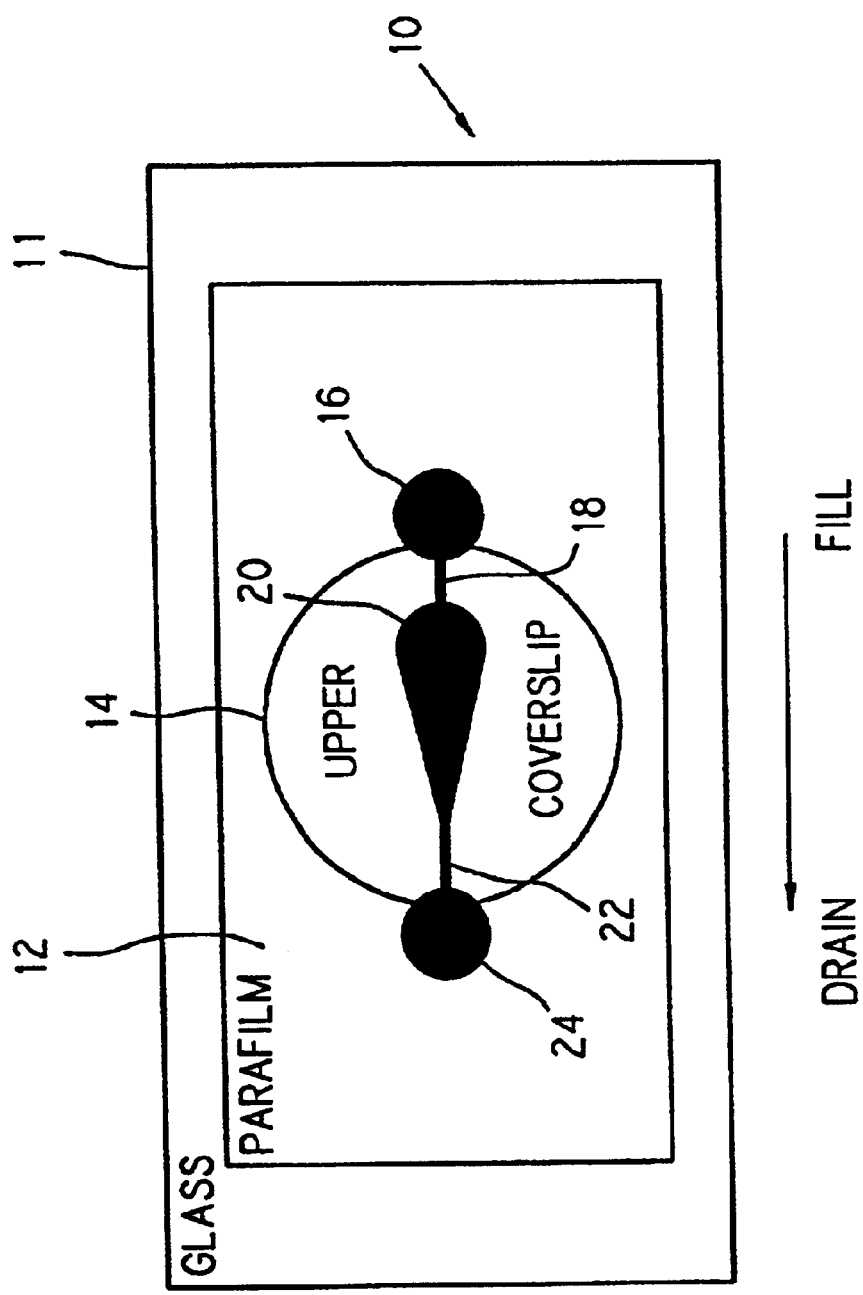
FIG. 4 is a top view of a microchamber microscope slide.

Conversion and analysis of interphase nuclei to meiotic or mitotic chromosomes is facilitated using the microchamber microscope slide. Referring to FIG. 4, there is shown a microchamber microscope slide 10. The microchamber microscope slide allows very small amounts of expensive and hard to come by reagents to be used sequentially on nuclei in situ. For instance, isolated nuclei can be placed into central microchamber 20 which is formed tear-drop shaped, pretreated, swelled, converted to chromosomes, stained, and then read or analyzed without further centrifugation or complex manipulation.

A thin strip of PARAFILM® wax 12, or other appropriate water resistant plastic tape or like material, is annealed to a standard microscope slide 11 or coverslip 14. The microscope slide 11 is generally flat and rectangular-shaped with a top and bottom side. The coverslip 14 is generally flat and circular-shaped with a top and bottom side. The PARAFILM® strip defines three wells connected by two narrow channels. Center microchamber 20 is generally teardrop-shaped with a generally rounded head end and a generally arrow shaped tail end. The volume of the microchamber is preferably between 5 $\mu l$ and 50 $\mu l$, most ideally between 10 $\mu l$ and 20 $\mu l$.

The head end of microchamber 20 is connected to a fill well 16 by a narrow entrance channel 18. The tail end of microchamber 20 is connected to a drain well 24 by a narrow exit channel 22. The volume of the resulting wells is determined by the thickness of PARAFILM® strip 12 and the size and shape of the wells; these parameters are adjustable.

Microchamber 20 is covered by a thin inverted coverslip 14. A thin inverted coverslip is best suited for use with an upright compound microscope. Other types of coverslips may be used. For example, an optically thin coverslip is suited for use with an inverted compound microscope.

In the preferred mode of operation, coverslip 14 completely covers microchamber 20 leaving fill well 16 and drain well 24 substantially uncovered. A sample of cells, nuclei, or other material, is pipetted to the wide part of the microchamber. The microchamber is then covered with a coverslip which is caused to adhere to the upper surface of the PARAFILM® strip 12 by applying two small drops of paraffin oil. The overlaying coverslip can be siliconized to minimize sticking of water and other materials to this surface.

Microchamber 20 is filled by capillary action by placing fluid in fill well 16. Excess fluid is then removed from both the fill well and drain well 24. The microchamber is flushed by placing fluid in the fill well and then sucking the fluid through the microchamber by capillary action achieved by touching blotting paper to the edge of the drain well.

The general teardrop shape enhances flushing of microchamber 20. For a 10 $\mu l$ microchamber as little as 20 $\mu l$ of fluid is sufficient to clear the microchamber. If necessary, the coverslip 14 can be removed and the fill channel 18 and exit channel 22 sealed with a small bead of silicone stopcock grease. Material can then be recovered from the microchamber.

The microchamber microscope slide is extremely versatile. It can be sterilized, placed in tissue culture medium, and used as a growing surface for cells. Further, it is possible to increase the depth of the two side wells while leaving the microchamber shallow. Each of the side wells could be covered with their own lid. One of the side wells could be filled several millimeters deep with tissue culture medium while the other well is left unfilled. Tissue culture medium would then flow through the microchamber across the cells until the two side wells reach equilibrium, the exact flow rate being adjustable. Further potential uses include the following: (1) analysis of growing cells; (2) analysis of isolated cells, particularly fetal blood cells; (3) analysis of cell nuclei, or other subcellular particles, organelles or materials; and (4) analysis of material of non-living origin.

The microchamber microscope slide allows analysis of material by essentially all light microscopy staining techniques including the following: (1) fluorescent microscopy of incorporated precursors, antibody staining, nucleic acid hybridization techniques; (2) conventional histological staining procedures; and (3) staining based on enzymatic amplification of molecular signals.

The microchamber microscope slide also allows analysis of biological material by incorporation of radioactive precursors, followed by autoradiographic detection of the incorporated precursors.

The microchamber microscope slide also allows "on-line" microscopic observation of material being treated or altered by fluids flowing through the microchamber. In particular, the microchamber microscope slide is ideally used to both isolate and analyze fetal cell from maternal blood. Isolation may be achieved by first coating the microchamber with the appropriate antibody to fetal cells, or their already isolated nuclei, and the microchamber is otherwise not sticky. The microchamber itself selects and holds the fetal cells, or nuclei, while the maternal cells, or nuclei, are washed away. The fetal cells, or nuclei, can then be fluorescently tagged in situ and their positions identified even before starting in vitro nuclear swelling and chromosome formation. The fetal cells or nuclei, can then be activated using the appropriate treatments described herein.

VIII. Activation Kits

The technology disclosed in the present invention can be used to produce activation kits useful for clinical activation of nuclei and scientific research. These kits are particularly useful for prenatal screening. Uses of an activation kit to aid in scientific research include facilitating the study of complex biochemical activities including the assembly of nucleosomes and chromatin on plasmid or viral DNA, formation of eukaryotic nuclear envelopes surrounding nuclear templates, semi-conservative replication of double stranded DNA within eukaryotic nuclei, conservative repair replication of single stranded DNA independent of nuclear envelope assembly, activation of quiescent cell nuclei, nuclear envelope breakdown, condensation of chromatin into chromosomes, formation of meiotic and mitotic spindles, regulated transcription of eukaryotic genes, and protein synthesis.

A basic activation kit comprises frozen activating egg extract and frozen CSF extract. These extracts are prepared based upon the methods described in the present invention. Preferably the kit contains frozen activating egg prepared from eggs having an elevated DNA synthesis activation activity. More advanced kits contain various supplements which aid in activation. The various supplements are either in separate containers present in the frozen activating egg extract or frozen CSF extract.

Preferably, these supplements are in separate containers. Useful supplements includes $CaCl_2$, nocodazole, $\beta$-glycerol-$PO_4$, phosphodiesterase inhibitor (e.g., caffeine), cAMP, protein kinase inhibitor (e.g., DMAP). Preferably, the activation kit contains a microchamber microscope slide.

The activation kits could also be supplemented with reagents used to study activation in general or determine the extent of genome replication. Useful supplements for these activities include radioactive nucleotides, biotinylated nucleotides and different dyes (e.g., biotin-Texas Red streptavidin and Hoechst).

IX. Cloning Whole Animals from Somatic Cell Nuclei

The procedures disclosed by the present invention, to activate nuclei, are also useful for preparing a nucleus for subsequent transplantation into an egg for the purpose of directing the development of a new organism. Prior to nuclear transplantation, the nucleus to be transplanted is activated in vitro. The activated nucleus is then transplanted into an egg whose own nucleus has either been removed or functionally inactivated. The egg subsequently develops into an new organism under the direction of genetic information contained in the transplanted nucleus. Uses of cloning somatic cell nuclei include, creation of a clone of genetically identical animals, cloning animals having favorable attributes, and producing more animals which are in danger of becoming extinct.

A difficulty in cloning somatic cell nuclei from mammalian species is that these nuclei are imprinted with patterns of gene structure and function (e.g., DNA methylation patterns) which differ from sperm and egg nuclei patterns. Thus, it is necessary to reprogram somatic cell nuclei before cloning to eliminate the different patterns. Prior activation of somatic cell nuclei in an appropriate egg extract before transplanting should allow for the necessary reprogramming to enable a transplanted nucleus to give rise to either a complete, or substantially complete new organism.

Cloning using a somatic cell nucleus comprises three steps; (1) activating the somatic cell nucleus, (2) preparing a recipient egg, and (3) transplanting the somatic cell nucleus into the egg. The first step is preferably carried out using the improved procedures, disclosed above, to activate a nucleus. Preferably isolation, pretreatment, further pretreatment, and contact with activating egg extract are preformed under conditions where the activated nucleus has a high DNA synthesis activation activity.

Preparation of a recipient egg will vary depending upon the egg source. The egg source should be treated in a manner to prevent activation before nuclear transplantation. Procedures to prepare mammalian eggs, such as those described by Martin et al. supra, are know in the art.

Preparation of a recipient egg includes destroying the egg's pronucleus. Destruction or removal of the egg's own nucleus guarantees that the eggs genetic material (DNA) does not contribute to the growth and development of the newly cloned individual. One method of destroying the pronucleus is by using ultraviolet light as described by Gurdon, in METHODS IN CELL BIOLOGY, XENOPUS LAEVIS:PRACTICAL USES IN CELL AND MOLECULAR BIOLOGY, 36:299–309, Academic Press, California. (Kay and Peng eds., 1991). Alternatively, the egg pronucleus can be surgically removed by procedures known in the art such as those described by King, in METHODS IN CELL PHYSIOLOGY 2:1–36, Academic Press, New York (D. M. Prescott, ed., 1966), and McGrath and Solter, Science 220:1300–1319 (1983).

Nuclear transplantation can be carried out by standard techniques. These techniques, vary depending upon the species, and are known in the art.

It should be possible to clone Xenopus in the following manner: nuclei from Xenopus red blood cells are isolated, pretreated, and further pretreated. Nuclei are then activated by contact with an activating egg extract. The nuclei are then activated to different stages in the cell cycle (e.g., S-phase, G2, etc.), and transferred to recipient prepared Xenopus eggs.

Recipient Xenopus eggs are prepared for nuclear transplantation by hardening using $Ca^{2+}$ (as described above), and then irradiating with ultraviolet light to destroy the egg's genome. One to two activated somatic nuclei, in 20 to 50 nanoliters are then microinjected into the Xenopus egg, into the clear cytoplasmic region that lies approximately 400 microns below the animal pole of the egg. The egg is then incubated under conditions that permit cytoplasm rotation. These conditions can be conveniently obtained by floating the egg on Metrizamide®. Rotation of the egg cytoplasm relative to the egg cortex is important for establishment of the proper dorsal/ventral axis of the developing vertebrate embryo.

X. EXAMPLES

Example 1

Further Induction Optimization

This example describes additional experiments carried out to further determine the optimal induction time for an activating egg extract. Protein synthesis during the early part of the first cell cycle in activated eggs or egg extracts is required for preparation of an activating extract capable of efficient and complete genome replication. The required proteins can either be synthesized in intact eggs before preparation of extracts or in extracts including frozen/thawed extracts. As noted above, activating egg extract should be prepared from extracts induced for more than 10 minutes to enhance DNA synthesis activation activity.

It was found that proteins synthesized during the first 28–30 minutes in intact eggs (incubated at 20° C.) or during the first 60–80 minutes in a freshly prepared and activated extract (incubated at 25° C.), promote subsequent DNA replication. In contrast, proteins synthesized later in the first cell cycle, i.e., after replication is underway, inhibit DNA synthesis. The changes in DNA synthesis can be detected as alterations in the time which DNA synthesis starts, the initial rate of replication, and the overall amount of replication.

The amount of $CaCl_2$ used to induce a freshly prepared CSF extract regulates whether or not the extract exits meiotic metaphase, traverses the first interphase, and re-enters the first M-phase. As judged by measurements of histone H1 kinase activity, fresh CSF extract induced by the addition of 3 mM $CaCl_2$ exits meiotic metaphase, enters interphase, but fails to enter mitosis-I. In contrast, CSF extract induced with 1.2 mM $CaCl_2$ exits meiotic metaphase, enters interphase, and then proceeds into mitosis-I, as indicated by a second peak in H1 kinase activity.

For the purpose of comparison, extracts were prepared from eggs induced and incubated at 20° C. for varying lengths of time before being crushed. In all cases the eggs were amassed, induced, washed, crushed, and extracts were prepared as described for prepared activating extracts with the following modifications: (1) all tubes and pipette tips used to prepare egg extracts were first treated with 1% diethylpyrocarbonate to destroy ribonuclease activity and (2) all the steps in extract preparation were carried out using plastic gloves to avoid ribonuclease contamination. Extracts were frozen on an aluminum block, chilled with liquid nitrogen. and then thawed at a later time prior to being used. DNA synthesis was followed by incorporation of $P^{32}dCTP$, followed by electrophoresis and phosphoimager analysis.

The results demonstrate that optimal DNA synthesis activating extracts are obtained by synchronously inducing batches of eggs and incubating them for 28–30 minutes at 20° C. Of the time periods tested the 28–30 minute extracts initiated nuclear replication earliest, synthesized DNA fastest, and replicated more DNA, then egg extracts induced for 10 minutes, 22 minutes, 34 minutes or 40 minutes. The overall order for earlier nuclear replication, faster DNA synthesis, and extent of DNA replication was as follows: 10 minutes<22 minutes<25 minutes<28 minutes>34 minutes>40 minutes. Because the cell cycle of the egg is so rapid, even small differences in the length of incubation period or the temperature of incubation result in suboptimal extracts.

It was also determined that maximal replication, even in the frozen/thawed 28–30 minute extract, depends on continuing protein synthesis during the first 30 minutes of the in vitro incubation. Activating egg extract were prepared as described above, induced for 28 minutes. Cycloheximide was added just prior to induction, or 30 minutes after induction. Maximal DNA replication was observed for control (no cycloheximide) and cycloheximide added 30 minutes after induction, while zero minute cycloheximide addition resulted in significantly less DNA replication. This suggests that the proteins required for efficient replication are relatively unstable but are abundantly synthesized from mRNAs recruited onto polysomes during the first 28–30 minutes following egg induction.

Example 2 cAMP Supplemented Activating Egg Extract

The affect of cAMP on DNA replication in activated *Xenopus* red blood cells was determined. *Xenopus* nuclei were isolated and pretreated by a method based on Coppock et al., *Developmental Biology* 131:102 (1989), as follows: *Xenopus* blood was obtained from females by cardiac puncture and collected using a syringe half-filled with Barth's solution (88 mM NaCl, 2.3 mM KCl, 0.82 mM $MgCl_2$ and 10 mM Hepes, pH 7.4) containing heparin (10 mg/ml); the blood was immediately diluted into 10 ml of ice-cold 0.6×SSC (1×SSC is 0.15 M NaCl, 0.015 M Sodium citrate, pH 7.0) containing 0.1 mg/ml heparin, 0.1 mM TPCK (N-tosyl-L-phenylalanine chloromethyl ketone), 0.1 mM TLCK (Nα-p-Tosyl-L-lysine chloromethyl ketone), 0.05 mM PMSF (phenylmethylsulfonyl fluoride), 5 µg/ml leupeptin, and 31.25 mM $Na_2S_2O_5$; bleeds containing clots, even small ones, were rejected; diluted blood was underlaid with 0.5 volumes of ice cold Metrizamide® (refractive index of 1.3660 in 0.6×SSC) and centrifuged at 180 g for 10 minutes at 4° C., red blood cells pelleted below Metrizamide® while white cells banded above Metrizamide®; the red cell pellet was resuspended using 0.6×SSC and centrifuged in Metrizamide® four more times to obtain erythrocytes of greater than 99.9% purity; cells were washed three times in NIB and resuspended at $2 \times 10^8$ cells/ml; cells were then resuspended in NIB:glycerol (7:3) and frozen in aliquots of 100 µl in liquid nitrogen; before using, frozen cells were thawed, diluted to $4 \times 10^7$ cells/ml in NIB at 23° C., and added to an equal volume of NIB containing 80 µg/ml lysolecithin (40 µg/ml final concentration) and 0.6 µg/ml trypsin (0.3 µg/ml final concentration) (the trypsin used in this example, and the other examples described herein, was Sigma brand Type XIII trypsin, TPCK treated from Bovine Pancrease, approximately 11,000 units/mg solid); after 5 minutes lysolecithin and protease treatment was stopped by adding soybean trypsin inhibitor to a concentration of 30 µg/ml and bovine serum albumin to a final concentration of 0.4%; the resulting nuclei were centrifuged at 800 g at 0° C. for 10 minutes, washed twice in NIB, resuspended with ice-cold NIB and kept on ice.

Isolated and pretreated nuclei were added at 200 nuclei/µl to 550 µl thawed "prepared activating egg extract" supplemented with 5 µg/ml nocodazole, 250 µg/ml cycloheximide, 10 µCi $P^{32}$-dCTP, 10 mM creatine phosphate, and 10 µg/ml creatine phosphokinase. Cyclic-AMP was then added to separate aliquots to yield final concentrations of 0.0 µM, 0.1 µM, 1.0 µM, or 10 µM.

Each aliquot was warmed to 23° C. and sampled over time to determine $P^{32}$-dCTP incorporation into replicated DNA. At each time point, a 7 µl aliquot was taken, frozen on dry ice, and later thawed and digested by the addition of 10 µl replication sample buffer (80 mM Tris (pH 8.0), 8 mM EGTA, 0.13% phosphoric acid, 10% Ficoll, 5% SDS, 0.2% bromphenol blue) containing proteinase K (1.0 mg/ml) for 2 hours at room temperature. Incorporated radioactivity was analyzed by electrophoresis on a 0.8% agarose gel (50V, 20 hours) followed by vacuum drying the gel and counting on a Betascope.

As indicated by Table 2, the addition of 10 µM cAMP inhibits DNA replication in activated nuclei as compared to DNA replication occurring without any cAMP. DNA replication increased with 0.1 µM and 1.0 µM cAMP. A greater increase was seen with 1.0 µM than with 0.1 µM cAMP. Thus, cAMP can be used to increase the activation activity of activating egg extracts. A concentration of approximately 0.3 µM, was used in subsequent studies.

TABLE 2

| Cpm Incorporated | Micromoles of Cyclic AMP Added | | | |
|---|---|---|---|---|
| After X Minutes | 0.0 | 0.1 | 1.0 | 10 |
| 0 | 14 | 14 | 10 | 43 |
| 45 | 37 | 51 | 14 | 34 |
| 90 | 73 | 68 | 56 | 31 |
| 135 | 288 | 290 | 564 | 35 |
| 180 | 839 | 1,141 | 2,316 | 85 |
| 240 | 1,556 | 2,945 | 4,484 | 168 |
| 300 | 2,954 | 2,692 | 5,504 | 571 |

Example 3

Caffeine Supplemented Activating Egg Extract

The effect of caffeine on DNA replication in activated *Xenopus* red blood cells was determined. The experimental conditions used were as described in Example 1 with the following changes: the concentration of cAMP was set at 0.3 µM and caffeine was added to the activating egg extract to a concentration of either 0.2 mM, 1.0 mM, or 5.0 mM.

As illustrated by FIG. 1, caffeine at 1.0 mM in the presence of 0.3 µM cAMP gave the highest initial rate and extent of DNA replication in activated nuclei. Thus, caffeine can increase the activation activity of an activating egg extract.

Example 4

CSF Extract Supplemented with DMAP and Treated with Activating Extract

Addition of 6-dimethylaminopurine (DMAP) to CSF extracts was used to further pretreat *Xenopus* erythrocyte nuclei and stimulate subsequent DNA replication in activating egg extract. DMAP can be used to inhibit nucleic acid synthesis and protein kinase activity. *Xenopus* erythrocyte nuclei were isolated and pretreated as described in Example 1 above, and incubated in thawed "prepared CSF extract" supplemented with 80 mM β-glycerol-PO$_4$, and 5 µg/ml nocodazole at a concentration of 2000 nuclei/µl. Further pretreatment was carried out by incubation for 30 minutes at 4° C., then 30 minutes at 25° C., then 60 minutes at 4° C. Half the samples were supplemented with 5 mM DMAP before addition of the nuclei. After the two hours of incubation, each sample was diluted with 9 volumes of activating egg extract, supplemented with 5 µg/ml nocodazole (this dose of nocodazole slows down the rate of replication) and approximately 160 µCi/ml P$^{32}$-dCTP. Aliquots were removed over time to measure DNA replication.

Figure 2:
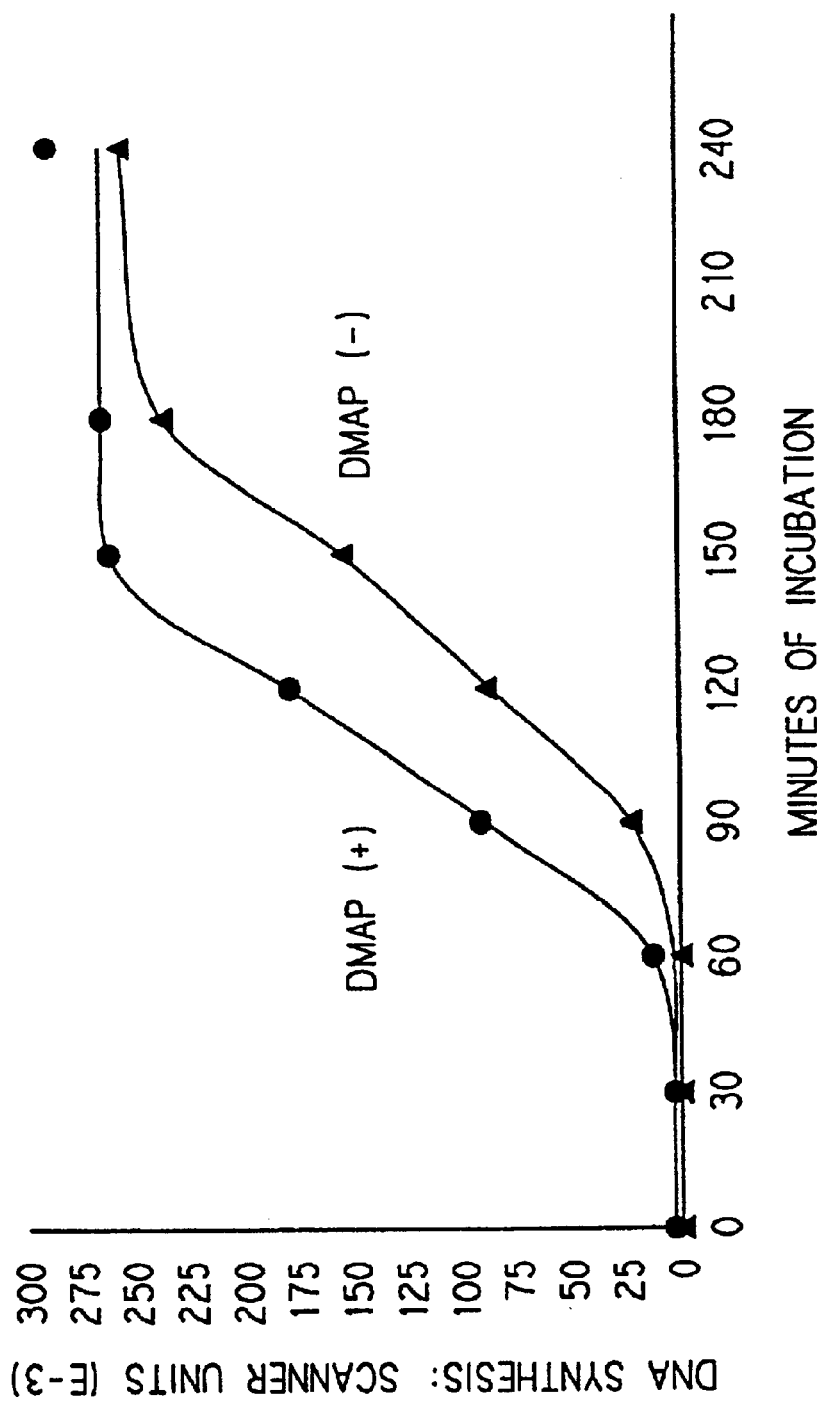
FIG. 2 shows the effect on DNA replication of activated nuclei, of using CSF extract supplemented with 6-dimethylamino-purine (DMAP).

As illustrated by FIG. 2, the addition of DMAP to CSF extracts enhanced the ability of the CSF extract to stimulate subsequent DNA replication in activating egg extract. DMAP decreased the lag time before the onset of replication and increased the initial rate and total amount of DNA synthesis.

Example 5

Warm-Then-Cold Regime

Various warm-then-cold regimes used as part of a further pretreatment increased DNA replication in activated nuclei. Thawed *Xenopus* erythrocyte nuclei (isolated and pretreated as in Example 1 above) were added at 2000 nuclei/µl to thawed "prepared CSF extract," supplemented with 80 mM β-glycerol-PO$_4$. The mixture was incubated using various warm-then-cold regimes. At the end of each incubation period samples was diluted with 9 volumes of "prepared activating egg extract" supplemented with 5 µg/ml nocodazole and P$^{32}$-dCTP. Samples were removed over time to measure the extent of DNA replication.

Figure 3:
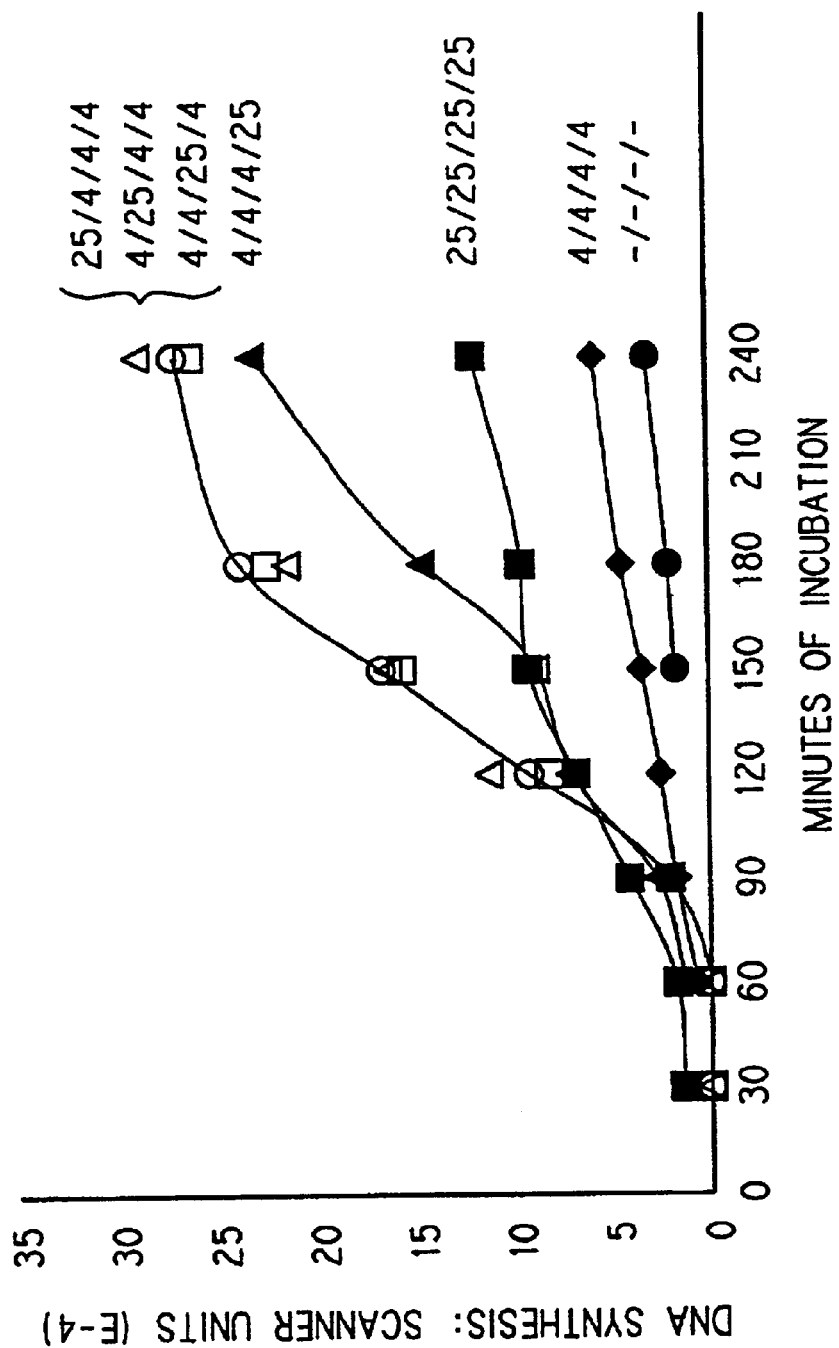
FIG. 3 shows the effect of various warm-then-cold protocols on DNA replication in activated nuclei.

As shown by the data represented in FIG. 3, the following warm-then-cold regimes stimulated subsequent DNA replication: 30 minutes at 25° C., and 90 minutes at 4° C.; 30 minutes at 4° C., 30 minutes at 25° C., and 60 minutes at 4° C.; 60 minutes at 4° C., 30 minutes at 25° C., and 30 minutes at 4° C. Incubation for 90 minutes at 4° C., and 30 minutes at 25° C. was not as effective as incubation regimes that had a warm period followed by a cold period. Thus, nuclei activation is preferably performed using a warm-then-cold regime.

Example 6

Activation Using Frozen/Thawed Extracts

Activation of *Xenopus* red blood cell nuclei was studied using frozen/thawed CSF extracts and frozen/thawed activating egg extract. *Xenopus* red blood cell nuclei were isolated and pretreated as described in example 1. These nuclei were further pretreated at 2000 nuclei/µl in thawed "prepared CSF extract" supplemented with 10 mM creatine phosphate, 10 µg/ml creatine phosphokinase, 5 µg/ml nocodazole, 80 mM β-glycerol-PO$_4$, 100 µM CaCl$_2$ and incubated using a warm-then-cold format of 60 minutes at 25° C. followed by 60 minutes at 4° C.

After further pretreatment, samples were diluted with 9 volumes of thawed "prepared activating egg extract" containing 10 mM creatine phosphate, 10 µg/ml creatine phosphokinase, and incubated with either: A) 200 µCi/ml P$^{32}$-dCTP; B) 16 µM biotin-11-dUTP, 16 µM MgCl$_2$; or C) no additions.

At various time intervals an aliquot of each incubation was treated as follows:

A) P$^{32}$-labelled samples were treated with sodium dodecyl sulfate (SDS), proteinase-K, and then analyzed on agarose gels to determine DNA replication. Total incorporated radioactivity was measured using a Molecular Dynamics phosphoimager. The sizes of the radioactive molecules were observed and photographed on X-ray film.

B) Biotin labelled nucleic acid was used to visualize replicated nuclear DNA. Biotin labelled samples were fixed by mixing into the samples approximately 40 volumes of freshly prepared 1.0 mM ethylene glycol bis-(succinic acid N-hydroxysuccinimide ester) (EGS) and incubating at 37° C. for 30 minutes. Fixed nuclei were stored at 8° C. for 48 hours and then centrifuged onto glass coverslips (2000 rpm, at 4° C. for 15 minutes) through a 25% glycerol layer. The glycerol layer was removed and the samples were stained with Texas Red-Streptavidin (Gibco BRL, diluted 1:40 in PBS). Coverslips were then washed with buffered saline and stained with 1.0 µg/ml Hoechst 33258 stain (for total DNA). Each sample was examined and photographed at 60x using an Olympus optical system. Using these conditions: 1) nuclear envelopes were detected under phase optics as a dark line around the nucleus; 2) total nuclear DNA was observed under fluorescent optics as Hoechst positive (blue) staining; and 3) newly replicated biotinylated DNA were detected as Texas Red positive (red) staining.

C) Samples from incubate (C) were used to measure histone H1 kinase activity during the course of the experiment.

As judged by both P$^{32}$-dCTP incorporation and biotinylated-dUTP incorporation, new DNA replication in erythrocyte nuclei was highly synchronous and efficient. Replication began at 30–40 minutes of incubation and was completed by 80–90 minutes of incubation. No additional DNA synthesis was observed between 90–140 minutes. After 140 minutes DNA replication resumed. The initial rate of DNA synthesis in this system using a frozen/thawed activating egg extract is only slightly slower than that using fresh activating egg extract. Furthermore, it appears that replication of the entire genome was achieved.

As judged by nuclear morphology and staining, swelling was observed about 20 minutes after addition of activating egg extract (T=20). At T=20 no DNA replication was observed. DNA synthesis and biotinylated-dUTP incorporation were both first observed at T=40. Nuclear swelling continued until T=80 at which time nuclear condensation and nuclear envelope breakdown began. Photographs of 10 or more nuclei at each time point revealed that virtually all nuclei in each sample were activated at the same time and in the same manner. Hoechst staining and biotin labelling revealed that nuclear DNA was first highly compacted (T=0), became more diffuse during the period of swelling and replication (T=20 to T=80), and then condensed into chromosome like structures (T=100 to T=180). Nuclear envelope breakdown occurred at T=100 to T=120 minutes, but mitotic spindle formation was not observed in these samples. This was likely due to the presence of low levels of nocodazole (0.5 µg/ml). At T=160 many of the nuclei appeared under phase contrast to have nuclear envelopes suggesting they entered a second interphase. All nuclei at T=180 had distinct chromosome-like structures indicating that they entered a second mitosis. DNA synthesis (P$^{32}$-dCTP incorporation) resumed between T=140 and T=160 and then stopped at T=160 in accord with a second S-phase followed by a second mitosis.

Histone H1 kinase levels were low at the start of S-phase (T=40) and rose gradually thereafter. Correlations of DNA synthesis, nuclear morphology, and H1 kinase levels suggested that a threshold level of H1 kinase leading to nuclear envelope breakdown and first mitosis was reached at T=100. H1 kinase levels continued to rise until T=180, despite the fact that DNA synthesis resumed at T=140–160.

First mitosis occurred relatively early (T=100 to T=120) and was not accompanied by DNA fragmentation. These observations are consistent with the view that genome replication was complete in this experiment. Agarose gel analysis of the $P^{32}$-labelled DNA demonstrated that virtually all newly synthesized DNA was initially of very high molecular weight (HMW), some of this material was then converted to pieces of a rather uniform moderate molecular weight (MMW). DNA pieces of the MMW size are not degradation products and reflect a fundamental unit of DNA packaging in condensing chromosomes. MMW may be due to experimental interruption of topoisomerase II dependent deconcatenation of replicated DNA loops.

In summary this experiment demonstrates, an in vitro system using frozen/thawed CSF extracts, and frozen/thawed activating egg extracts prepared from *Xenopus* eggs. In this system nuclei swell, acquire new envelopes, and cycle through at least one complete S phase followed by one complete M phase. Only a limited amount of DNA synthesis takes place in a second S-phase. This system permits highly synchronous activation and cycling of quiescent cell nuclei, and is directly applicable to the activation of non-dividing human cells such as fetal cells including keratinocytes, trophoblasts, erythrocytes and leukocytes, and sperm nuclei.

Example 7

Comparison of High Speed Versus Low Speed CSF Extract

This example compares nuclei activation using a pretreatment in either low speed or high speed "prepared CSF extract." Activation was carried out using frozen/thawed activation extract induced for 28 minutes. Nuclei activation was assayed by measuring DNA replication and Histone H1 kinase activity.

*Xenopus* erythrocyte nuclei were prepared as described in Example 2 and incubated in either a low speed prepared "CSF extract" or a high speed "prepared CSF extract." In both cases nuclei were then diluted into 9 volumes of a 28 minute induced activating egg extract. For each incubate one set of samples were collected to measure histone H1 kinase activity, another set of samples containing $P^{32}$-dCTP was used to measure DNA synthesis. The nuclei incubated in the high speed CSF extract replicated and progressed through the cell cycle more synchronously than those incubated in low speed CSF extract.

Example 8

Use of Diluted CSF Extract Supplemented with DMAP

This example illustrates the use of diluted CSF extract supplemented with DMAP to achieve nuclear envelope formation and nuclear structure in the absence of DNA synthesis. *Xenopus* erythrocyte nuclei were isolated and pretreated using lysolecithin and trypsin as described in Example 2 above. "Prepared CSF extract" was made using high speed centrifugation and frozen by spotting the extract, made 7.5–10% (v/v) glycerol, as a 20 µl droplet onto a block of aluminum immersed in liquid nitrogen. Aliquots of the extract were thawed on ice and supplemented with 10 mM creatine phosphate, 10 µg/ml creatine phosphokinase, 80 mM β-glycerol-$PO_4$, and 0.1 mM $CaCl_2$. While still on ice the CSF extract received a small volume ($\frac{1}{33}^{rd}$) of DMAP to a final concentration of 5 mM, and was then diluted with different amounts of EB buffer as follows: mixture 1, 100%=extract only no EB; mixture 2, 75%=3 volumes extract+1 volume EB; mixture 3, 50%=1 volume extract+1 volume EB; and mixture 4, 25%=1 volume extract+3 volumes EB.

Each of these mixtures was warmed to 25° C. and incubated for 15 minutes. Pretreated nuclei were then added in $\frac{1}{10}$ the volume to a final concentration of 2000 nuclei/µl. Samples from each incubate were taken immediately (0), 60, 90, 120 minutes later and fixed, examined, and photographed. Nuclei treatment with diluted CSF-DMAP resulted in greater swelling than nuclei treated with undiluted CSF-DMAP. Nuclei treated with mixture 3 had a larger extent of nuclear swelling, nuclear envelope formation, and chromatin decondensation, than nuclei treated with the other mixtures. Additional experiments using $P^{32}$-dCTP and biotinylated-dUTP demonstrated that no DNA synthesis took place during the process of nuclear swelling described above.

Example 9

Use of Diluted CSF Extract Supplemented with DMAP, $MgCl_2$ and EGTA

This example illustrates the effect of diluted CSF extract supplemented with DMAP, $MgCl_2$ and EGTA on nuclear envelope formation, swelling, and chromatin structure. Nuclei were treated as described in Example 7 prior to the addition of CSF extract. The CSF extract (prepared as in Example 7), while still on ice was supplemented as follows: 5 mM DMAP, 16 µM Biotinylated-dUTP and 16 µM $MgCl_2$. The supplemented extract was diluted with an equal volume of EB buffer containing 5 mM potassium EGTA, pH 7. This mixture was warmed to 25° C. and incubated for 15 minutes. Pretreated nuclei were then added in $\frac{1}{10}$ the volume to a final concentration of 2000 nuclei/µl. Samples from each incubate were taken immediately 0, 15, 45, 60, and 90 minutes later and were fixed, examined, and photographed.

The 50% CSF-DMAP, supplemented with EGTA and $MgCl_2$, caused pretreated erythrocyte nuclei to rapidly swell and acquire a nuclear envelope. No biotin incorporation into DNA was observed. Thus in contrast to Example 7, swelling took place in the absence of DNA synthesis. In addition, the DNA observed in this example was more compacted than the DNA observed in example 8. The difference between this example and example 8 is likely due to the alteration of CSF extract cation concentration, and composition. For example, the EGTA may chelate the $Ca^{2+}$ thereby lowering the $Ca^{2+}$ while additional $Mg^{2+}$ is added to increase the $Mg^{2+}$ concentration.

Example 10

Microchamber Microscope Slide

This example illustrates the use of the microchamber microscope slide to analyze and activate nuclei. *Xenopus* erythrocyte nuclei were isolated and pretreated as described above in Example 1. These nuclei, in NIB buffer, were allowed to settle onto the lower surface of several microchamber microscope slides. A coverslip was placed over each sample and sealed using oil along the sides. Nuclei were further pretreated using thawed "prepared CSF extract" made 80 mM in β-glycerol-PO$_4$ and supplemented with 10 mM creatine phosphate and 10 μg/ml creatine phosphokinase. Ten microliters of CSF extract was allowed to flow into each well and the microchamber microscope slide was then subjected to the following warm-then-cold treatment; 30 minutes on ice, 30 minutes at 25° C., and 30 minutes on ice. After the warm-then-cold treatment, the CSF extract in each well was displaced by the addition of 20 μl freshly "prepared activating egg extract" containing biotinylated-dUTP. The microchamber microscope slides were then warmed to 25° C. At varying lengths of time the incubations were stopped by rinsing the microchamber with 75 μl of an appropriate buffer containing Texas red streptavidin (for detection of incorporated biotin), followed by staining with Hoechst stain for detection of total DNA. The nuclei were photographed at a magnification of 60× using fluorescent optics.

Red blood cell nuclei before pretreatment were small and compact. The majority of nuclei were separated from one another indicating they were not damaged or clumped during isolation.

Red blood cell nuclei at the end of further pretreatment in CSF extract were attached to the surface of the microchamber microscope slide and remained small and highly compact.

Red blood cell nuclei 30 minutes after addition of activating egg extract swelled dramatically, and were attached to the surface of the slide. Texas red streptavidin staining of these nuclei demonstrated the lack of DNA replication.

Nuclei after 85 minutes of incubation in activating egg extract were swollen. As seen by Texas red streptavidin staining, these nuclei were surrounded with a nuclear envelope and initiated DNA replication.

After 150 minutes of incubation in fresh activating egg extract DNA replication was complete and the nuclei entered mitosis. As a result of entering mitosis, the nuclear envelopes dissembled and the DNA condensed into chromosome-like structures which remained attached to the surface of the microchamber microscope slide.

These results demonstrate the utility of a microchamber microscope slide in nuclei activation. Using the methods and products disclosed in the present invention nuclei were conveniently activated on a microchamber microscope slide.

Example 11

Activation of Nuclei from Fetal Red Blood Cells Isolated from the Umbilical Cord The activation of human fetal red blood cells using activating egg extract is described below. Human fetal red blood cells were prepared from umbilical cord blood, pretreated with lysolecithin and trypsin, and contacted with activating egg extract.

Human fetal red blood cells were isolated from umbilical cord blood and fractionated into a nucleated cell fraction and a non-nucleated cell fraction as described by Bianchi et al., Proc. Natl. Acad. Sci. USA 87:3279 (1990). A sample of neonatal umbilical cord blood was drawn into a vacuum tube containing anticoagulants, the blood was diluted 1:1 with Hank's balanced salt solution (HBSS) (Hanks and Wallace, Proc. Exo. Biol. Med. 71:196 (1949)), layered over a Ficoll/ Hypaque column (Pharmacia) and spun at 1400 rpm for 40 min at room temperature. The mononuclear cell layer was recovered and washed twice by centrifugation in-HBSS. The cells were then washed several times in NIB buffer (250 mM sucrose, 25 mM NaCl, 10 mM Pipes, 1.5 mM MgCl$_2$, 0.5 mM spermidine, and 0.15 mM spermine, pH 7.0); the resulting cell pellet was suspended in NIB:Glycerol (7:3) and frozen in liquid nitrogen as 100 μl aliquots containing 6.3×10$^6$ cells.

Frozen cells were thawed at room temperature and put on ice, washed twice with NIB, diluted to 4×10$^7$ cells/ml in NIB at 23° C., and added to an equal volume of NIB containing 80 μg/ml lysolecithin and 0.6 μg/ml trypsin; lysolecithin and trypsin treatment was halted after 5 minutes by adding soybean trypsin inhibitor to a concentration of 30 μg/ml and bovine serum albumin to a final concentration of 0.4%. Isolated nuclei were added directly to thawed "prepared activating egg extract" to a concentration of 200 nuclei/μl, supplemented with 10 mM creatine phosphate, 10 μg/ml creatine phosphokinase, 5 μg/ml nocodazole, 0.3 mM cAMP, and 1 mM caffeine. One aliquot of this sample was supplemented with P$^{32}$-dCTP at approximately 200 μCi/ml and used to measure DNA replication. A second aliquot was sampled periodically for fluorescent microscopic examination of nuclei after fixation and staining with Hoechst dye (as described above).

Human red blood cell nuclei treated in the manner described above swelled significantly during the first 90 minutes and initiated DNA synthesis. DNA synthesis continued for approximately 4.0 hours after which nuclear chromatin condensed. However, the observed kinetics of DNA synthesis indicated that complete genome replication was not achieved in this experiment. The failure to achieve complete genome replication was probably due to the failure to further pretreat the isolated human nuclei in CSF extract and because activating egg extract contained a relatively high level of nocodazole, i.e., 5 μg/ml.

Despite the difficulties encountered, the formation of metaphase chromosomes demonstrates that the present invention can be used to activate non-dividing human nuclei. The non-dividing human nuclei activated analogously to Xenopus erythrocyte nuclei. Therefore, the various improvements described in the present invention, such as further pretreatment in CSF extract, a warm-then-cold regime and the addition of 100 μM CaCl$_2$, which result in increasing the activation of non-dividing Xenopus erythrocyte are applicable to activate non-dividing human nuclei.

Example 12

Activation of Nuclei of Fetal Red Blood Cells Isolated from Fetal Liver

This example illustrates the use of the products and methods described herein to determine preferred activation conditions and activate blood cells isolated from fetal liver. Mononucleated cells isolated from fetal liver, studied in this example, were predominately fetal blood cells as judged by their red color. The following steps were preformed:

Step 1: Isolation of mononucleated human liver cells. Mononucleated human cells were isolated from human fetal liver by gently trimming the tissue and then homogenizing it between two glass slides. The cells were collected by suspension in phosphate buffered saline and then transferred to a centrifuge tube. 2 ml of Ficoll was layered under the cell suspension which was then centrifuged at 2000 rpm for 20 minutes. The red mononuclear cells (upper layer) containing predominantly erythroid blood cells were collected, diluted with phosphate buffered saline and centrifuged gently to pellet the cells. Cell pellets were resuspended and pelleted one more time in phosphate buffered saline and then resuspended in RPM1 tissue culture medium.

The cells were frozen in liquid nitrogen. To prepare cells for freezing in liquid nitrogen, the cells were pelleted by gentle centrifugation, resuspended, and centrifuged again in Hank's balanced salt buffer containing protease inhibitors (TPCK 0.1 mM, TLCK 0.1 mM, PMSF 0.05 mM, and leupeptin 5 µg/ml) at 4° C. The resulting supernatant was clear indicating the absence of hemolysis. The pellet was resuspended in 1–1.5 ml of NIB containing protease inhibitors (TPCK 0.1 mM, TLCK 0.1 mM, PMSF 0.05 mM, and leupeptin 5 µg/ml), the volume was brought to 10 ml. The suspension was then spun at 1000 rpm for 10 minute at 4° C., again no hemolysis was observed, and resuspended to final volume of 5 ml in NIB containing protease inhibitors (TPCK 0.1 mM, TLCK 0.1 mM, PMSF 0.05 mM, leupeptin 5 µg/ml). The concentration of cells was approximately $3.55 \times 10^7$/ml. The cells were then spun down, resuspended in 1.775 ml 70% NIB-30% glycerol, and frozen as 50 µl aliquots in liquid nitrogen.

Step 2: Membrane permeabilization of nuclei.

The membrane of nuclei prepared as described in step 1 was permeabilized using lysolecithin. Frozen cells were warmed quickly, diluted with NIB, and lysed by addition of lysolecithin at a final concentration of 40 µg/ml for 5 minutes at 25° C. At this point the nuclei are surrounded by a cytoskeletal matrix and do not expand or divide if contacted with activating extract.

Step 3: Removal of cytoskeletal proteins surrounding the nucleus and nuclear matrix proteins within the nucleus.

The nuclei from step 2 were treated with trypsin using variable amounts of enzyme and treatment times. Increasing the length of trypsin treatment from 0–15 minutes, at 25° C., increased the extent of DNA synthesis after standard CSF pretreatment and replication in activating extract. Incubation times longer than 15 minutes resulted in decreased replication, probably due to nuclear damage and clumping. Optimal trypsin pretreatment used 0.4 µg/ml trypsin for 15 minutes at 25° C. However, as would be appreciated by one skilled in the art, conditions for trypsin treatment may vary depending on how the cells are washed to remove protease inhibitors added during cell preparation and the trypsin incubation temperature. These results confirm that, human cell nuclei, like the *Xenopus* erythrocyte system, should be prepared for activation using a controlled proteolytic step.

The lysolecithin-trypsin pretreatment was stopped by adding BSA to 0.4%+soybean trypsin inhibitor to a final concentration of 30 µg/ml followed by gentle centrifugation. The nuclear pellet was suspended and pelleted once more in 0.4% BSA and then in NIB alone.

Step 4: Further pretreatment with CSF extract.

Washed nuclei were further pretreated in CSF extract to enhance activation. Pretreatment as described in steps 2 and 3 was not sufficient to allow swelling and replication of nuclei using frozen/thawed activating extracts. This was attributed to the absence of MPF activity in frozen/thawed activating extract. Indeed, pretreatment with CSF extract substantially increased responsiveness of lysolecithin/trypsin pretreated nuclei.

CSF extract further pretreatments were also preformed using varying lengths of time and temperature. Frozen/thawed CSF extract were supplemented with 10 mM creatine phosphate, 10 µg/ml creatine phosphokinase, 80 mM β-glycerol-PO$_4$, and 0.1 mM CaCl$_2$. H1 kinase levels in such extracts were high and stable for several hours.

An incubation for 60 minutes at 25° C. followed by 60 minutes at 4° in CSF extract was found to give the highest amount of activation. Incubations at 25° C. for longer than 60 minutes resulted in lower DNA synthesis, probably because individual nuclei break up into separate chromosomes. Nuclei in these experiments were at 2000/µl, but a broad range of concentrations should be equally effective.

Additional experiments carried out using *Xenopus* erythrocytes suggest that the 60 minute cold incubation after the 60 minute warm step increases the rate of subsequent replication. Possibly, the cold step disassembles spindles containing microtubules that form around nuclei during the warm step.

Thus, the CSF is preferably supplemented with 10 mM creatine phosphate, 10 µg/ml creatine phosphokinase, 80 mM β-glycerol-PO$_4$, and 0.1 mM Ca$^{2+}$, and a treatment regime involving incubation for 60 minutes at 25° C. followed by 60 minutes at 4° C. is used in nuclei further pretreatment.

Step 5: Activation of erythroid cell nuclei. Nuclear swelling, envelope formation, and replication were carried out on human fetal liver erythroid cell nuclei prepared using the optimal conditions described in steps 1–4 above. The nuclei were activated by diluting the further pretreated nuclei into nine volumes of prepared activating extract (prepared from eggs activated for 30 minutes and supplemented with 10 mM creatine phosphate, and 10 µg/ml creatine phosphokinase, plus 16 µM biotinylated-dUTP or 0.2 µCi/µl αP$^{32}$-dCTP). The resulting nuclei concentration was about 200/µl.

The following measurement were taken: DNA synthesis was monitored using extract containing P$^{32}$dCTP by gel electrophoresis; histone H1 kinase was measured; and samples, labelled with biotinylated-dUTP were taken for cytological analysis of DNA replication and nuclear envelope breakdown.

DNA synthesis began after a lag of 30 minutes and continued until 120 minutes. Little or no round-2 DNA synthesis occurred between 150–180 minutes, probably because nuclear envelope breakdown had not taken place. Second mitosis began between 180–210 minutes as seen by the rise in H1 kinase activity, and was accompanied by fragmentation of the DNA.

Analysis of the size of the replicated DNA demonstrated that the molecules were initially very large, but at the time that DNA synthesis stopped (120 minutes) a substantial portion of the DNA was converted to a middle molecular weight (MMW) band of approximately 50 kilobases. Subsequent experiments have demonstrated that formation of this band coincides with onset of mitosis, even in the absence of a significant histone H1 kinase peak, as is the case in this experiment. We believe that the MMW DNA band is an artifact generated by SDS-proteinase K disruption of the topoisomerase II-DNA complexes involved in chromosome condensation. Daughter strand deconcatenation is a mandatory part of chromosome condensation and of necessity requires Type-II topoisomerase (Topo II) breakage of the replicated chromosome at many sites. Thus we believe that our in vitro conditions allow the normal G2-like period to take place following the S-phase. Chromosome condensation and deconcatenation takes place during this period.

The process of DNA fragmentation process is distinct from chromosome condensation and MMW band formation. Fragmentation appears to occur when nuclei enter mitosis without having completed DNA synthesis, i.e., premature chromosome condensation.

Cytotological analysis demonstrated that little or no nuclear envelope breakdown occurred in this experiment at 120–150 minutes, also in accord with the absence of a histone H1 kinase peak. Extensive nuclear swelling began about 30 minutes after incubation. Nuclear envelopes formed between 30 and 60 minutes and biotin labelling of new DNA began by 60 minutes. The intensity of biotin labelling increased during the S-phase, in keeping with $p^{32}$ labelling. Maximum swelling with chromatin dispersion was reached at about 90 minutes, while some condensation of chromatin took place at about 90–120 minutes although a small amount of DNA synthesis was still on going. In the period 120–150 minutes there was marked chromatin condensation suggesting the onset of mitotic prophase, but nuclear envelope breakdown did not take place.

The 90 minute sample was further analyzed to determine the extent of sample homogeneity. The first 36 nuclei detected with Hoechst stain were photographed. In replicated nuclei Texas red staining of biotin bleeds through into the blue Hoechst channel turning the nuclei purple. About 40% of the nuclei failed to swell and failed to replicate. Almost all remaining nuclei swelled and replicated to the full extent. There were very few partially replicated nuclei. The inability of some of the nuclei to replicate was attributed to nuclear damage since the response of carefully prepared frog erythrocyte nuclei is much more homogeneous.

Experiments were also carried out to determine whether nuclear swelling was dependent on DNA synthesis, by activating nucleic in the presence of aphidicolin (added at T=0). Biotin labelling confirmed that no replication took place in the aphidicolin treated nuclei. The results demonstrated that even in the absence of replication many nuclei swelled significantly.

Step 6: Formation of mitotic chromosomes.

Swelled and replicated nuclei were treated with Cyclin-Δ90 or CSF extract. Cyclin-Δ90 was added to activating extract to obtain prophase mitotic chromosomes, while CSF extract was added to obtain metaphase chromosomes and nuclear envelope breakdown.

Addition of $\frac{1}{20}^{th}$ volume of cyclin-Δ90 at T=100 (minutes) caused a slight but real improvement in the clarity of prophase chromosomes observed in T=120 nuclei and thereafter seemed to increase the extent of chromosome condensation. Nuclear envelope breakdown was observed at T=240 and separate, chromosome-like were released.

Addition of ½ volume of CSF extract at T=100 caused a rapid extensive condensation of DNA and disappearance of the nuclear envelope. This state of condensation remained stable until T=240.

Example 13

Activation of Human Sperm Nuclei Using a PPT Pretreatment

This example illustrates the use of a permeabilization-protease-thiol reducing agent (PPT) pretreatment to enhance activation of human sperm nuclei. Fresh semen from a healthy male donor was obtained, diluted in an equal volume of yolk test buffer (Jasjey, D. G. and Cohen, M. R. *Fertility Sterility* 35:205–212, 1981) and frozen in liquid nitrogen in approximately 1 ml aliquots containing approximately $1\times10^8$ sperm of which approximately 68% were motile.

On the day of the experiment, sperm samples were thawed at room temperature and washed twice in ice cold NIB buffer by centrifugation. Sperm were then permeabilized by incubation in 100 μg/ml lysolecithin for 5 minutes at 25° C. and then treated with 100 μg/ml trypsin (e.g., a protease) for 10 minutes at the same temperature. The lysolecithin/trypsin treatment was stopped by the addition of soybean trypsin inhibitor to 30 μg/ml and dialyzed/lyophilized bovine serum albumin to 0.4% and then washed by centrifugation. The sperm were then incubated in a solution of 5 mM dithiothreitol (DTT) (e.g., a thiol reducing agent) in 5 mM in NIB for 60 minutes on ice and then post-treated with 1 mM N-ethylmaleimide in NIB for 10 minutes at 25° C. A final wash was carried out in NIB and the nuclei were resuspended at 40,000/μl. Two additional aliquots were prepared as described above except that in one case the DTT was omitted from the 60 minute incubation in NIB, and in the other case the trypsin was omitted during the 10 minute incubation following lysolecithin treatment.

Each of the above three samples were then added at a final concentration of 4000/μl to a frozen/thawed preparation of high speed "prepared CSF extract" that had been supplemented with 10 mM creatine phosphate, 10 μg/ml creatine phosphokinase, 80 mM β-glycerophosphate, and 0.1 mM $CaCl_2$. Nuclei were incubated for 90 minutes at 25° C. and then for 60 minutes at 4° C.

Each of the three CSF extract treated samples were then diluted with 9 volumes of a frozen/thawed 25 minute activated egg extract supplemented with 10 mM creatine phosphate, and 10 μg/ml creatine phosphokinase, plus 16 μM biotinylated-dUTP and 16 μM $MgCl_2$, or plus 0.2 μCi/μl $\alpha P^{32}$-dCTP. Each sample was incubated at 25° C. and sampled periodically by either fixed staining for biotin incorporation into DNA and photographed, or fractionated on agarose gel and counted for incorporation of label nucleotides into DNA.

Cytology demonstrated that each of the three treatment regimes resulted in swelling of the sperm nuclear DNA, but only the combined lysolecithin-trypsin-DTT pretreatment procedure resulted in new nuclear envelope formation, extensive spherical swelling of the nucleus, and new DNA synthesis. DNA synthesis as determined by $P^{32}$-dCTP incorporation also demonstrated that only the combined lysolecithin-trypsin-DTT pretreatment procedure resulted in significant replication. The combined lysolecithin-trypsin-DTT pretreatment procedure brought more than a 5 fold increase in DNA synthesis than pretreatments with lysolecithin and trypsin or lysolecithin and DTT.

Additional cytological analysis and in situ hybridization was carried out using two nucleic acid probes; one to a reiterated sequence on the X-chromosome and one to a single copy sequence on chromosome 18. The lysolecithin-trypsin-DTT pretreated and activated sperm nuclei were recovered after 120 minutes of incubation in activating extract in the presence of biotinylated-dUTP. Two nuclei were stained for total DNA (Hoechst=blue), the X-chromosome (using a digoxygenin-labelled probe-green), newly synthesized biotinylated DNA (Texas-red streptavidin=red), and chromosome 18 (using a biotinylated probe+Texas-red streptavidin=red dots). The intensity of the Hoechst staining and the biotinylated-dUTP staining in the first nucleus was less than that in the second nucleus. This demonstrates that first nucleus had only begun in vitro replication while the second nucleus had replicated more completely. In addition, the first nucleus contained only one copy of the X-chromosome, indicating that the probed region of the chromosome had not yet replicated, while the second nucleus contained two copies of the X-chromosome, indicating that it had replicated by this time. In addition, two copies of chromosome 18 were detected in the first nucleus, suggesting that this probe detects an early replicating sequence. Detection of chromosome 18 was obscured in the in the second nucleus by the higher level of incorporated biotinylated-dUTP.

These results are consistent with the notion that both thiol reduction and protease induced changes in the sperm cytoskeleton and protamines are required for displacement of protamines and their replacement by chromatin forming histones in the egg extracts. Chromatin assembly is important in the formation of the surrounding nuclear envelope and completion of the envelope is important for initiation of DNA synthesis. These results also demonstrated that human sperm cell nuclei which have been activated and replicated in vitro can be used for genetic analysis.

Additional experiments demonstrated that the optimized protocol described above also resulted in formation of mitotic chromosomes from human sperm nuclei.

Other embodiments are within the following claims.

What is claimed is:

1. A product for swelling an animal cell nucleus without causing DNA synthesis comprising
   a) a cytoplasmic extract from at least one animal egg arrested in meiotic metaphase II of the cell cycle,
   b) a protein kinase inhibitor, and
   c) an aqueous buffer containing a monovalent cationic salt.

2. The product of claim 1 wherein said extract is a supernatant from a high-speed centrifugation.

3. The product of claim 2 wherein said extract is frozen and thawed prior to use.

4. The product of claim 1 wherein said extract is frozen and thawed before use.

5. The product of claim 1 wherein said at least one animal egg is a plurality of *Xenopus* frog eggs.

6. The product of claim 1 wherein the aqueous buffer has a pH between 6.5 and 7.5.

7. The product of claim 1 wherein the protein kinase inhibitor is 6-dimethylaminopurine.

8. The product of claim 7 wherein the protein kinase inhibitor is 6-dimethylamino purine.

9. The product of claim 1 wherein the monovalent cationic salt is potassium gluconate.

10. The product of claim 1 further comprising at least one ingredient selected from the group consisting of divalent cationic salts and agents that chelate divalent cations.

11. The product of claim 10 that includes ethylene glycol-bis ($\beta$aminoethyl ether) N, N,N',N'-tetraacetic acid.

12. A method for swelling a nucleus of an animal cell without causing DNA replication by incubating said nucleus in a product comprising:
    a) a cytoplasmic extract from at least one animal egg arrested in meiotic metaphase II of the cell cycle,
    b) a protein kinase inhibitor, and
    c) an aqueous buffer containing a monovalent cationic salt, wherein said incubating results in swelling of said nucleus.

13. The method of claim 12 wherein said cell nucleus is a human cell nucleus.

14. The method of claim 12 wherein said animal cell nucleus is separated from its surrounding cytoskeleton prior to being incubated in said product.

15. The method of claim 14 wherein said separation comprises permeabilizing said cell with a detergent and treating said cell with at least one reagent selected from the group consisting of proteases, polyanions and reducing agents.

16. The method of claim 12 wherein said product includes 6-dimethylamino purine and ethylene glycol-bis ($\beta$aminoethyl ether) N,N,N',N'-tetraacetic acid.

* * * * *

UNITED STATES PATENT AND TRADEMARK OFFICE
CERTIFICATE OF CORRECTION

PATENT NO. : 6,878,546 B2
DATED : April 12, 2005
INVENTOR(S) : Lawrence J. Wangh Ph.D.

It is certified that error appears in the above-identified patent and that said Letters Patent is hereby corrected as shown below:

Column 46,
Line 2, change "6-dimethylaminipurine." to -- an inhibitor of histone H1 kinase. --

Signed and Sealed this

Fifth Day of July, 2005

JON W. DUDAS
*Director of the United States Patent and Trademark Office*